United States Patent
Zhang

(10) Patent No.: US 11,664,119 B2
(45) Date of Patent: May 30, 2023

(54) METHOD AND SYSTEM FOR PROVIDING MEDICAL SERVICES

(71) Applicant: SHANGHAI UNITED IMAGING HEALTHCARE CO., LTD., Shanghai (CN)

(72) Inventor: Yi Zhang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 452 days.

(21) Appl. No.: 16/044,684

(22) Filed: Jul. 25, 2018

(65) Prior Publication Data

US 2019/0035501 A1    Jan. 31, 2019

(30) Foreign Application Priority Data

Jul. 25, 2017  (CN) .......................... 201710612835.6

(51) Int. Cl.
*G16H 40/20* (2018.01)
*G16H 80/00* (2018.01)
(Continued)

(52) U.S. Cl.
CPC .............. *G16H 40/20* (2018.01); *G16H 80/00* (2018.01); *G16H 10/60* (2018.01); *G16H 15/00* (2018.01); *G16H 30/20* (2018.01); *G16H 40/40* (2018.01)

(58) Field of Classification Search
CPC ........ G16H 10/60; G16H 15/00; G16H 30/20; G16H 40/20; G16H 40/40; G16H 80/00
See application file for complete search history.

(56) References Cited

U.S. PATENT DOCUMENTS 8,738,396 B2 * 5/2014 Green, III .............. G16H 10/20
705/2
9,754,127 B2   9/2017 Pfeiffer et al.
(Continued)

FOREIGN PATENT DOCUMENTS

CN          1354436 A    6/2002
CN        102004862 A    4/2011
(Continued)

OTHER PUBLICATIONS

First Office Action in Chinese Application No. 201710612835.6 dated Mar. 31, 2020, 20 pages.
(Continued)

*Primary Examiner* — Jay M. Patel
(74) *Attorney, Agent, or Firm* — Metis IP LLC

(57) ABSTRACT

The present disclosure provides a method and system for providing medical services to a user. The method may include acquiring first information of a medical process including a plurality of sub-processes to be allocated with medical resources. The method may also include obtaining second information on medical resources, and the second information may include available time slots and locations of the medical resources. The method may further include allocating the medical resources for the medical process based on the first information and the second information. The method may also include determining, for at least one sub-process of the plurality of sub-processes of the medical process, appointment information of the at least one sub-process based on at least a portion of the second information corresponding to the medical resource allocated to the at least one sub-process. The method may further include notifying, by the one or more servers via a network, the user with the appointment information of the at least one sub- (Continued)

process of the plurality of sub-processes in a designated manner.

20 Claims, 12 Drawing Sheets

(51) Int. Cl.
  *G16H 10/60* (2018.01)
  *G16H 15/00* (2018.01)
  *G16H 30/20* (2018.01)
  *G16H 40/40* (2018.01)

(56) References Cited

U.S. PATENT DOCUMENTS

| | | | |
|---|---|---|---|
| 9,959,512 B2 | 5/2018 | Camp et al. | |
| 10,354,211 B1* | 7/2019 | Pilkington | G16H 40/20 |
| 10,366,790 B2* | 7/2019 | Lynn | G16H 10/60 |
| 2005/0055252 A1* | 3/2005 | Todd | G06Q 10/02 |
| | | | 705/5 |
| 2006/0004605 A1* | 1/2006 | Donoghue | G16H 10/60 |
| | | | 705/2 |
| 2009/0164236 A1 | 6/2009 | Gounares et al. | |
| 2011/0257496 A1* | 10/2011 | Terashima | A61B 5/74 |
| | | | 600/347 |
| 2013/0129305 A1 | 5/2013 | Hsiao | |
| 2013/0231947 A1* | 9/2013 | Shusterman | G16H 40/67 |
| | | | 705/2 |
| 2014/0278480 A1 | 9/2014 | Baniameri et al. | |
| 2014/0324469 A1* | 10/2014 | Reiner | G16H 50/70 |
| | | | 705/3 |
| 2015/0112696 A1* | 4/2015 | Kharraz Tavakol | |
| | | | G06Q 10/06311 |
| | | | 705/2 |
| 2015/0339447 A1* | 11/2015 | Kitagawa | G16H 15/00 |
| | | | 705/2 |
| 2016/0098539 A1* | 4/2016 | Zamanakos | A61B 5/7275 |
| | | | 705/3 |
| 2016/0224737 A1* | 8/2016 | Okabe | G16H 40/63 |
| 2016/0283670 A1* | 9/2016 | Tubman | G06F 3/04847 |
| 2017/0112392 A1 | 4/2017 | Wu | |
| 2017/0286621 A1* | 10/2017 | Cox | G16H 50/20 |
| 2017/0293950 A1* | 10/2017 | Rathod | G06Q 30/0639 |
| 2017/0330193 A1* | 11/2017 | Tolson | C12P 7/26 |
| 2017/0369947 A1* | 12/2017 | Song | C12Q 1/6886 |
| 2018/0025117 A1* | 1/2018 | Kanada | G16H 10/60 |
| | | | 705/3 |
| 2018/0047091 A1* | 2/2018 | Ogden | G06Q 30/0261 |
| 2018/0052968 A1* | 2/2018 | Hickle | G16H 50/20 |
| 2018/0059895 A1* | 3/2018 | McLaren | G06F 3/04883 |
| 2018/0098728 A1* | 4/2018 | Cales | A61B 5/7264 |
| 2018/0136974 A1 | 5/2018 | Yang et al. | |
| 2018/0247272 A1* | 8/2018 | Cunico | H04L 67/306 |
| 2019/0355077 A1* | 11/2019 | Ahmed | G06Q 30/0611 |
| 2020/0051677 A1* | 2/2020 | Harrison | G06Q 20/108 |
| 2020/0251204 A1* | 8/2020 | Teodoro | G16H 10/60 |

FOREIGN PATENT DOCUMENTS

| | | |
|---|---|---|
| CN | 102496133 A | 6/2012 |
| CN | 103473631 A | 12/2013 |
| CN | 105787697 A | 7/2016 |

OTHER PUBLICATIONS

Wang, Yang et al., Design and Implementation of Liaoning Unified Appointment Platform, Chinese Journal of Health Informatics and Management, 12(1): 64-70, 2015.

Mwesigwa, Collins, An E-Health Tele-Media Application for Patient Management, 2013 IST-Africa Conference & Exhibition, 2014, 7 pages.

* cited by examiner

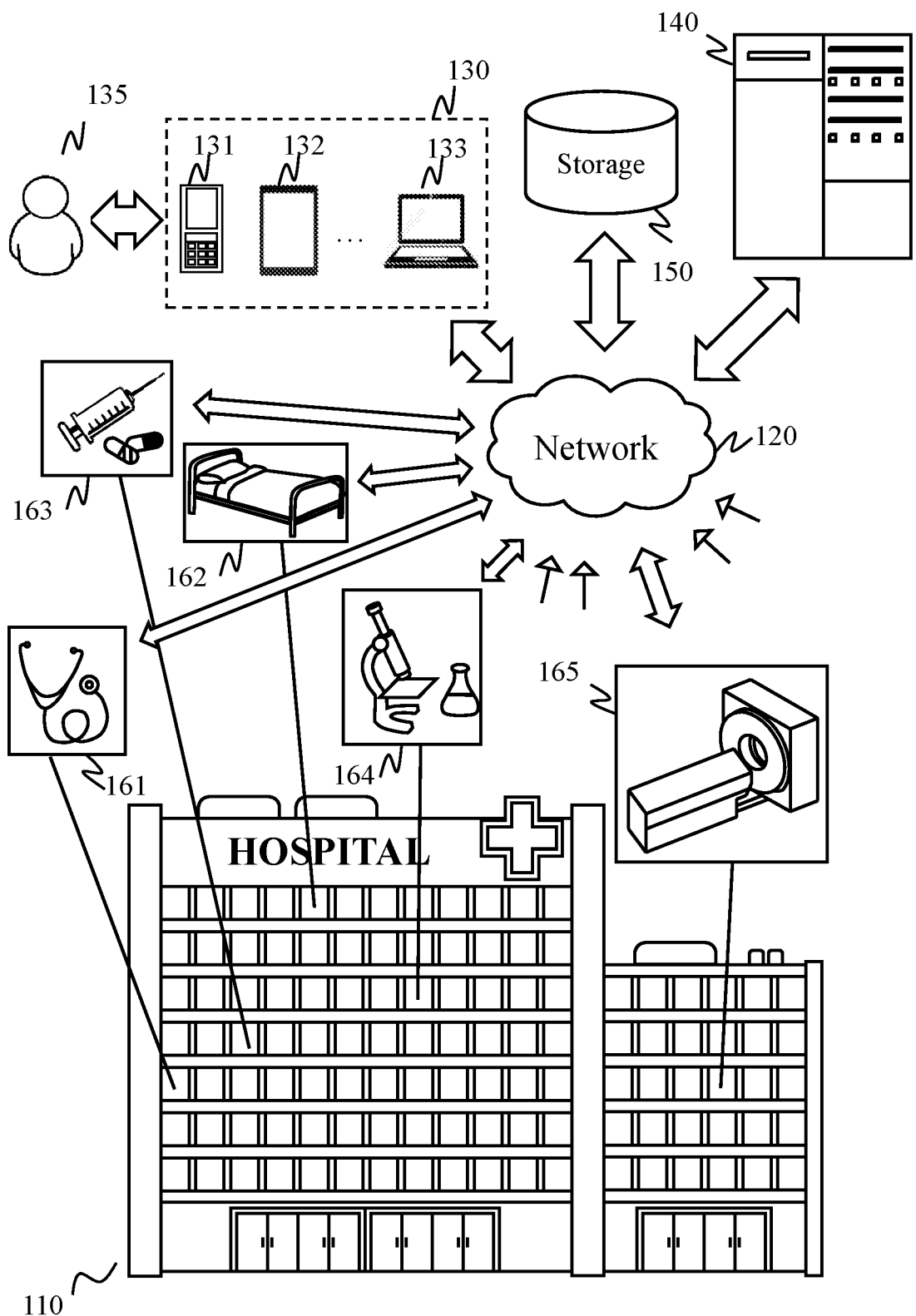
FIG. 1-A

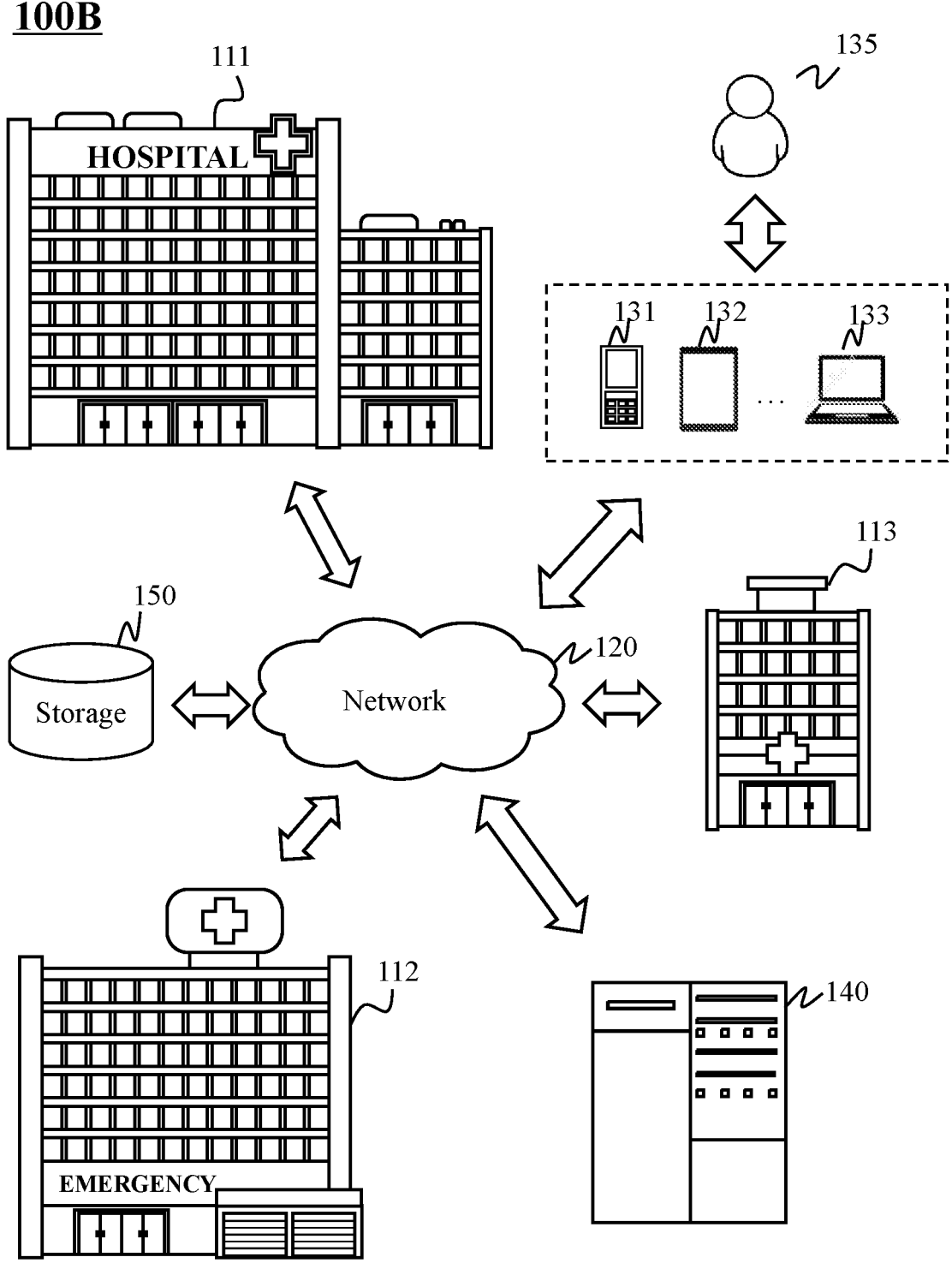
FIG. 1-B

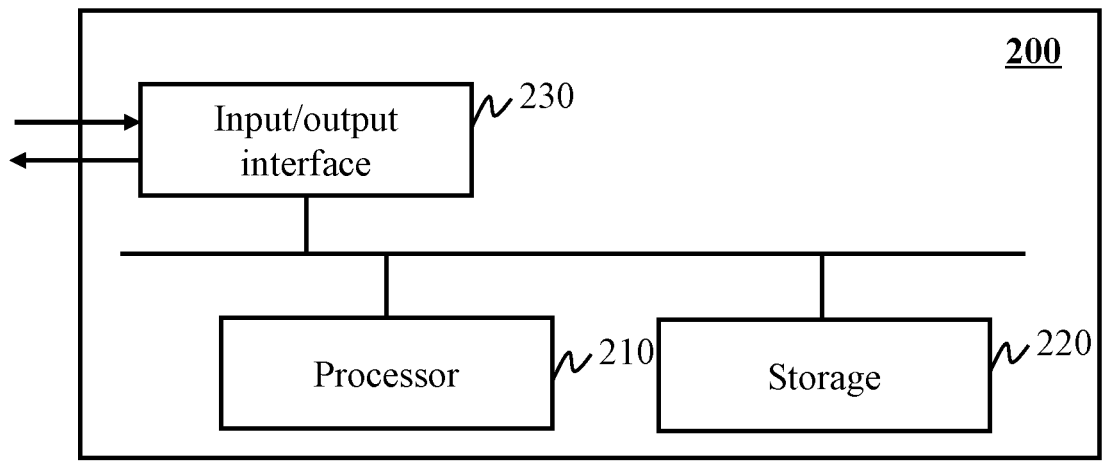
FIG. 2-A
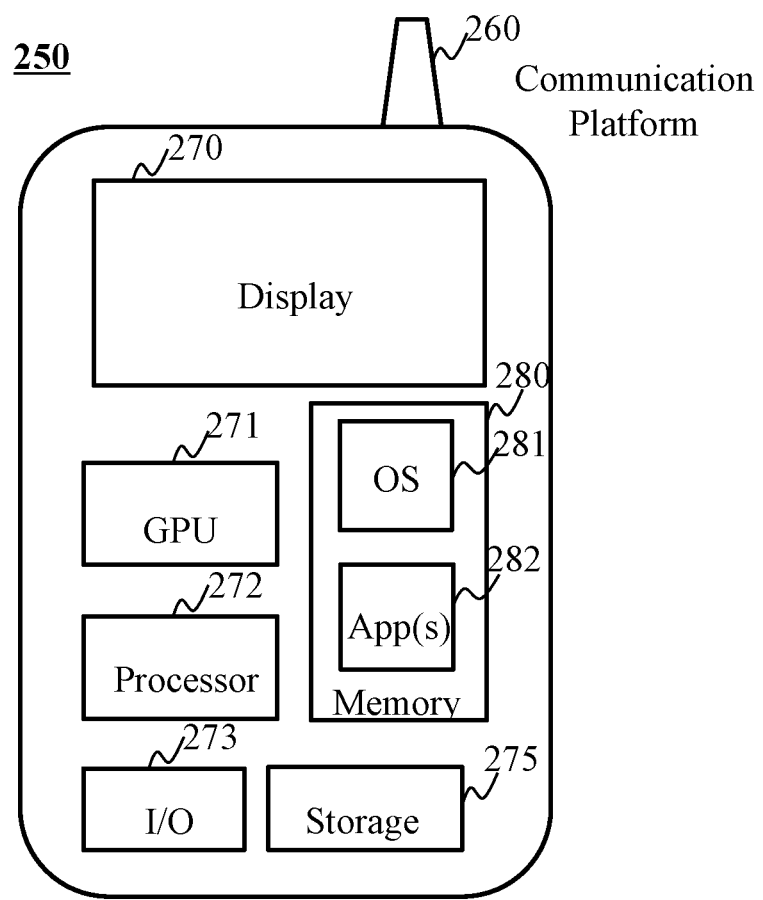
FIG. 2-B

METHOD AND SYSTEM FOR PROVIDING MEDICAL SERVICES

CROSS-REFERENCE TO RELATED APPLICATIONS

This application claims priority of Chinese Application No. 201710612835.6 filed on Jul. 25, 2017, the entire contents of which are hereby incorporated by reference.

FIELD

The present disclosure generally relates to a method and system for providing medical service, and more particularly to a method and system for allocating medical resources.

BACKGROUND

With the innovation and development of mobile technology, a great number of hospitals and medical centers nowadays have been digitalized to streamline diagnostic and therapeutic processes. The main businesses of a medical system, such as registering for medical services, outpatient services, inpatient services, electronic medical records (EMR), medical examinations, etc., have been managed and maintained using computing devices (e.g., computers) and networks (e.g., the Internet). To further increase the efficiency of such a medical system, there are needs for techniques to facilitate the information interaction between healthcare providers (e.g., doctors, nurses, specialists) and patients and to improve the utilization level of medical resources (e.g., doctors' time, medical imaging and/or treatment devices, etc.).

SUMMARY

Some embodiments of the present disclosure provide a method for providing medical services to a user. The method may include detecting a medical plan arrangement application executing on a mobile computing device. The medical plan arrangement application may automatically communicate with one or more servers over a network. The method may also include acquiring first information for identifying a medical process. The medical process may include a plurality of sub-processes. The method may further include acquiring, from at least one storage device, second information on medical resources of a plurality of medical resource providers. The second information may include available time slots of the medical resources. The method may also include communicating with the medical plan arrangement application executing on the mobile computing device to receive a medical resource allocation request. The method may further include, after receiving the medical resource allocation request, initiating a medical resource allocation process by programmatically executing a process as following: for each sub-process of at least some of the plurality of sub-processes: determining, based at least on the first information, a schedule time slot of the sub-process; determining, from the medical resources based at least on the second information, one or more candidate medical resources that satisfy a criterion of being available during the schedule time slot of the sub-process; selecting a target medical resource from the one or more candidate medical resources; and assigning the target medical resource to the sub-process. The method may also include, for at least one sub-process of the plurality of sub-processes that is assigned a selected medical resource, executing a notification process of the at least one sub-process by programmatically executing a process as following: determining appointment information of the at least one sub-process, wherein the appointment information may include information on the medical resource allocated to the at least one sub-process; encrypting first data corresponding to the appointment information of the at least one sub-process to be sent to the medical plan arrangement application; providing the encrypted first data to the medical plan arrangement application executing on the mobile computing device to generate a first presentation on a display of the mobile computing device, wherein the first presentation may include the appointment information of the at least one sub-process and provides a first user interface feature, and, from the first user interface feature, the user can trigger transmission of a navigation request to the one or more servers to initiate, by the one or more servers, a navigation process to determine a route to a location of the assigned medical resource of the at least one sub-process; and receiving, from the mobile computing device, the navigation request after the user interacts with the first user interface feature. The method may further include, after receiving the navigation request, initiating the navigation process by programmatically executing a process as following: determining, based on location data determined by the medical plan arrangement application executing to interface with a positioning module of the mobile computing device, a current location of the mobile computing device; determining, based on the second information, the location of the assigned medical resource of the at least one sub-process; determining a route from the current location of the mobile computing device to the location of the medical resource assigned to the at least one sub-process; and providing navigation data to the medical plan arrangement application executing on the mobile computing device to generate a second presentation including a map on the display of the mobile computing device, wherein the second presentation may depict, (i) the current location of the mobile computing device on the map, (ii) the location of the medical resource assigned to the sub-process on the map, and (iii) the route on the map. Some embodiments of the present disclosure also provide a system to perform the method and computer readable media that, when executed, causing the system to perform the method.

In some embodiments, the communicating with the medical plan arrangement application executing on the mobile computing device to receive a medical plan arrangement request may include: encrypting second data regarding the medical process to be sent to the medical plan arrangement application; providing the encrypted second data to the medical plan arrangement application executing on the mobile computing device to generate a third presentation on the display of the mobile computing device; and receiving, from the mobile computing device, the medical plan arrangement request after the user interacts with the first user interface feature. The third presentation may depict the medical process related to the patient and provides a second user interface feature from which the user can trigger transmission of the medical plan arrangement request to the one or more servers.

In some embodiments, the method may further include: determining an upcoming sub-process of the medical process as the at least one sub-process of the plurality of sub-processes for which the notification process is to be executed; and determining a notification time point before an attendance time slot of the upcoming sub-process with a predetermined time interval. The notification process of the upcoming sub-process may be executed at the notification time point.

In some embodiments, the second information may further include locations of the medical resources, and the method may further include: determining a location associated with the user; and determining distances from the location associated with the user to the locations of the medical resources, wherein the target medical resource is selected based at least on the determined distances.

In some embodiments, the selecting a target medical resource from the one or more candidate medical resources may include: encrypting third data regarding the one or more candidate medical resources to be sent to the medical plan arrangement application; providing encrypted third data to the mobile computing device via the network, causing the mobile computing device to generate a fourth presentation on a display of the mobile computing device, wherein the fourth presentation may include the one or more candidate medical resources corresponding to the sub-process and concurrently provides a third user interface feature from which the user can select a medical resource as the target medical resource from the one or more candidate medical resources and trigger a transmission of a selection request including the target medical resource; and receiving the selection request from the mobile computing device.

In some embodiments, the method may further include: receiving, from the mobile computing device through the network, a search request including time information; searching, in response to the received search request, an objective sub-process from the plurality of sub-processes based on the time information as the at least one sub-process of the plurality of sub-processes of which the notification process is to be executed.

In some embodiments, the medical resource allocation process may be executed based on one or more first rules of a rulebook, and the method may further include, when a sub-process of the plurality of sub-processes is failed to be allocated with a medical resource via the medical resource allocation process based on the one or more first rules: retrieving one or more second rules from the rulebook; and continuing to execute the medical resource allocation process for the sub-process based at least on the one or more second rules.

Some embodiments of the present disclosure provide a method for operating one or more servers to provide medical services to a user. The method may include acquiring, by one or more servers, first information of a medical process from a first storage device. The medical process may include a plurality of sub-processes to be allocated with medical resources. The method may also include obtaining, by the one or more servers, second information on medical resources from a second storage device. The second storage device may provide medical resource information of one or more medical resource providers, and the second information may include available time slots and locations of the medical resources. The method may further include allocating, by the one or more servers, the medical resources for the medical process based on the first information and the second information. The method may also include determining, by the one or more servers, for at least one sub-process of the plurality of sub-processes of the medical process, appointment information of the at least one sub-process based on at least a portion of the second information corresponding to the medical resource allocated to the at least one sub-process. The appointment information of the at least one sub-process may be for presentation on a user interface of a mobile computing device. The method may further include notifying, by the one or more servers via a network, the user with the appointment information of the at least one sub-process of the plurality of sub-processes in a designated manner. Some embodiments of the present disclosure also provide a system to perform the method and computer readable media that, when executed, causing the system to perform the method.

In some embodiments, the method may further include: determining an upcoming sub-process of the medic process as the at least one sub-process of the plurality of sub-processes whose appointment information is to be notified; determining a notification time point based on a closest time point associated with the upcoming sub-process; and notifying the user by sending to the mobile computing device via the network the appointment information of the upcoming sub-process for presentation on the user interface at the notification time node.

In some embodiments, the notifying the user with the appointment information of the at least one sub-process of the plurality of sub-processes in a designated manner may include: providing first data corresponding to the appointment information of the at least one sub-process of the plurality of sub-processes; and transmitting the first data to the mobile computing device via the network. The first data may cause the mobile computing device to generate a first presentation on a display of the mobile computing device, and the first presentation may include the appointment information of the at least one sub-process of the plurality of sub-processes.

In some embodiments, the method may further include: determining a location associated with the user; determining distances from the location associated with the user to the locations of the medical resources. The allocating the medical resources for the medical process may be based further on the determined distances.

In some embodiments, the method may further include: determining, based on location data received from the mobile computing device via the network, a current location of the mobile computing device; determining, based on the second information, a location of the allocated medical resource included in the first presentation; determining a route from the current location of the mobile computing device to the location of the allocated medical resource; and providing navigation data including the route to the mobile computing device to generate a second presentation including a map on the display of the mobile computing device. The second presentation may depict: (i) the current location of the mobile computing device on the map, (ii) the location of the allocated medical resource on the map, and (iii) the route on the map.

In some embodiments, the allocating the medical resources for the medical process based on the first information and the second information may include: determining, based at least on the first information, a schedule time slot of the at least one sub-process; determining, from the medical resources based on the first information and second information, one or more candidate medical resources that satisfy a criterion of being available during the schedule time slot of the at least one sub-process; selecting a target medical resource from the one or more candidate medical resources; and assigning the target medical resource to the at least one sub-process as the allocated medical resource of the at least one sub-process.

In some embodiments, the selecting a target medical resource from the one or more candidate medical resources may include: transmitting third data to the mobile computing device via the network, causing the mobile computing device to generate a fourth presentation on a display of the mobile computing device, wherein the fourth presentation includes the one or more candidate medical resources corresponding to the at least one sub-process and concurrently provides a user interface feature from which the user can select a medical resource as the target medical resource from the one or more candidate medical resources and trigger a transmission of a selection request including the target medical resource; and receiving the selection request from the mobile computing device.

In some embodiments, the medical resources may be allocated for the medical process based further on one or more first rules of a rulebook. The method may further include, when a sub-process of the plurality of sub-processes is failed to be allocated with a medical resource based on the one or more first rules: retrieving one or more second rules from the rulebook; and continuing to allocate medical resources for the sub-process based at least on the one or more second rules In some embodiments, the method may further include receiving, from the mobile computing device through the network, a search request including time information; searching, in response to the received search request, an objective sub-process from the plurality of sub-processes based on the time information as the at least one sub-process of the plurality of sub-processes of which the appointment information is to be notified.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTIONS OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 1-A and 1-B are schematic diagrams illustrating exemplary medical resources allocation system according to some embodiments of the present disclosure;

FIG. 2-A is a schematic diagram illustrating exemplary hardware and/or software components of an exemplary computing device;

FIG. 2-B is a schematic diagram illustrating exemplary hardware and/or software components of an exemplary mobile computing device;

DETAILED DESCRIPTION

Figure 3:
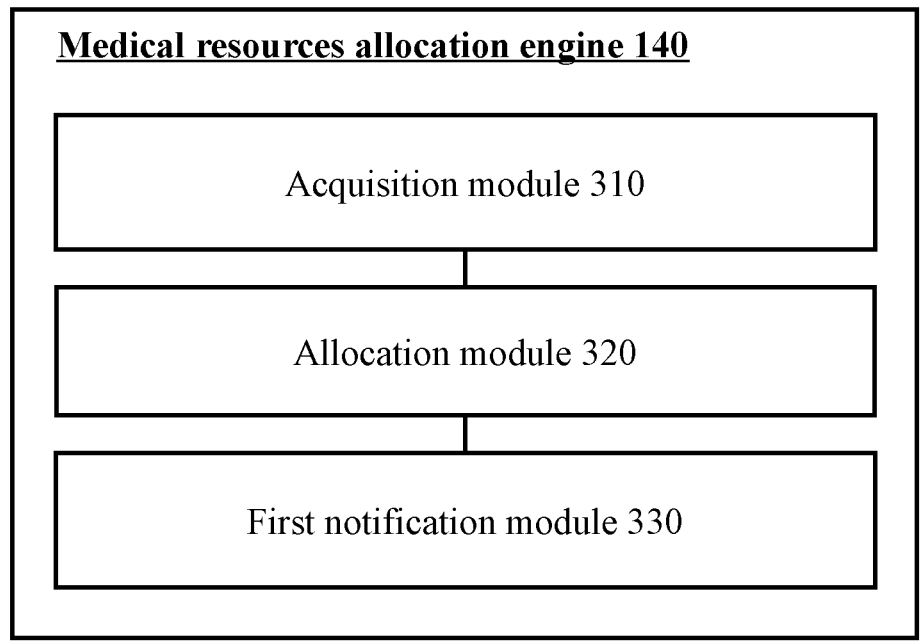
FIG. 3 is a schematic diagram illustrating an exemplary medical resources allocation device according to some embodiments of the present disclosure.

The present disclosure is directed to a method and system for allocating medical resources. The method and system may allocate medical resources based on medical processes automatically and/or according to a user instruction. The method and system may also notify a user with a medical process, the progress thereof, and the corresponding allocated medical resources in a specified or designated manner to provide the user with an intuitive view of the medical process, or the progress thereof.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Generally, the word "module," "sub-module," "unit," or "block," as used herein, refers to logic embodied in hardware or firmware, or to a collection of software instructions.

A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts.

Software modules/units/blocks configured for execution on computing devices (e.g., processor 210 as illustrated in FIG. 2-A) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure.

FIGS. 1-A and 1-B are schematic diagrams illustrating exemplary medical resources allocation system according to some embodiments of the present disclosure. The medical resources allocation system may include at least one medical resources provider (e.g., the medical resources providers 110 illustrated in FIGS. 1-A, and/or 111, 112, and 113 illustrated in FIG. 1-B), a network 120, one or more terminal devices 130, a medical resources allocation device 140, and storage 150.

The medical resources allocation system may be configured to allocate medical resources for a medical process of a user 135. The medical process used herein may include a diagnostic process, a therapeutic process, an examination process, a registration or check-in process, or the like, or a combination thereof. The medical process may include a plurality of sub-processes (e.g., creating the medical records or the user profile, first visit, examination (e.g., CT examination, blood test), second visit, treatment, follow-up examination, post treatment monitoring, or the like). Each of the plurality of sub-process may relate to one or more medical services or medical resources provided by one or more medical resources providers. By allocating medical resources for the medical process, each of the plurality of sub-process may be assigned with one or more corresponding medical resources.

The user 135 may be a patient, a doctor, a nurse, a specialist, an assistant who may assist in making an appointment for a patient or attending to the patient in a medical process. The user 135 may feed information to or receive information from the medical resources allocation device 140. Different users 135 may have different access privileges to the information on the medical resources managed by the medical resources allocation device 140. For instance, a patient user may view and/or input information regarding his own medical history and medical process(es) with the medical resources provider 110; a doctor may view and/or provide information (e.g., provide initial information and/or revise pre-existing information) regarding his own patients and their medical processes with the medical resources provider 110, medical resources needed or assigned to those patients or their medical processes; an assistant may view and/or provide information (e.g., provide initial information and/or revise pre-existing information) that is needed for making an appointment or attending to a patient in a medical process, e.g., information regarding multiple patients and their medical processes with the medical resources provider 110, medical resources needed or assigned to those patients or their medical processes. Different access privileges of different users 135 may be controlled or identified based on access credentials or login information.

In some embodiments, the user 135 may be a patient seeking for medical treatment. Through the medical resources allocation system described herein, the user 135 may manage his/her own medical process according to information on available medicals collected and provided by such a medical resources allocation system.

In some embodiments, the medical resources allocation system may be in the form of allocation system 100A as illustrated in FIG. 1-A. The allocation system 100A may be a built-in system of one medical resources provider (e.g., the medical resources provider 110) for medical resources management. The allocation system 100A may be configured to manage only the medical resources of the medical resources provider 110. The user 135 may acquire from the allocation system 100A information exclusive to the medical resources provider 110 and manage his medical process using the medical services and medical resources provided only by the medical resources provider 110.

In some embodiments, the medical resources allocation system may be in the form of allocation system 100B as illustrated in FIG. 1-B. The allocation system 100B may be shared by a plurality of medical resources providers (e.g., the medical resources providers 111, 112, 113) for medical resources management. In some embodiments, the allocation system 100B may be configured to manage the medical resources providers separately and/or independently. The user 135 may acquire from the allocation system 100B information exclusive to one medical resources provider (e.g., one of 111, 112, or 113) and manage his medical process using the medical services and medical resources provided only by that medical resources provider. In some embodiments, the allocation system 100B may be configured to manage and coordinate the allocation of the medical resources of multiple medical resources providers (e.g., at least two of 111, 112, and 113). The user 135 may acquire information from the plurality of medical resources providers and manage his medical process using the medical services and medical resources provided by the plurality of medical resources providers in his own will or based on the recommendation provided by his doctor or therapist. The doctor or therapist may be human or an intelligent device.

For demonstration purposes and simplicity, the allocation system 100A will be described in detail in the following text.

The medical resources provider 110 (as well as the medical resources providers 111, 112, and/or 113) may provide one or more medical services (e.g., diagnosis, therapy, testing) and the corresponding medical resources. The medical services provided by the medical resources provider 110 may include, for example, outpatient services 161 (e.g., clinic), inpatient services 162 (e.g., intense care unit (ICU) medical services, surgical services, emergency treatments), pharmacy and injection services 163, testing 164 (e.g., blood tests, urine tests), medical imaging services 165 (e.g., computed tomography (CT), medical resonance imaging (MRI), positron emission tomography (PET), digital radiography (DR)), or the like, or a combination thereof. The medical resources provider 110 (as well as the medical resources providers 111, 112, and/or 113) may be a hospital, a medical center, a clinic, a center for disease control, etc.

The medical resources provided by the medical resources provider 110 may refer to any human resources and/or equipment resources that may be used to provide one or more medical services to a patient. The medical resources may relate to, for example, information and/or availability of a medical device (e.g., type, utility status (e.g., idle, busy, reserved for a specific time slot, shutdown, disabled), location), a clinic (e.g., type(s) of medical services provided, available medical devices, business hours, location), a doctor or a technician (e.g., specialty, availability (office hours, available time slots (or idle time slots), etc.), office location(s)), one or more medicines (e.g., type, stock, location), hospital beds (e.g., availability, location) and surgical rooms (e.g., type, available devices, location, utilization status (busy, standby, ready for use, reserved for a specific time slot, idle, in maintenance)), or the like, or a combination thereof. During a medical process, one or more medical service may be involved. Each involved medical service may relate to a plurality of medical resources. Taking the medical imaging service 165 for example, the related medical resource may include the availability of an imaging room, an imaging device (e.g., CT), an imaging technician, or the like, or a combination thereof. A time slot in the present disclosure may include a start time point and at least one of an ending time or a time duration.

Information on the medical resources (or referred to as medical resource information) may be collected and updated in the medical resources allocation device 140 (e.g., through the network 120) according to information provided by the staff of the medical resources provider 110 (e.g., doctors, nurses, specialists). Alternatively or additionally, the devices providing specific medical services may collect and feed the information on the medical resources to the medical resources allocation device 140 automatically. The information updating may be performed by one or more specialized information acquisition devices (e.g., one or more terminal devices 130), and/or by the devices providing specific medical services (e.g., CT device, MRI device).

The information on the medical resources may include identity information (e.g., name, title, career, ID, serial number, brand, type, model, manufacturer, year in service), time information (e.g., available time slot(s), reserved time slot(s), time for maintenance), location information (e.g., address, room number, geographic coordinates), utilization information (e.g., busy, standby, shutdown, disabled), or the like, or a combination thereof.

In some embodiments, the medical resources provider(s) 110 may use at least one storage device (e.g., storage 150, a server) to store medical resource information. The storage device may store and/or provide medical resource information of one or more medical resource providers 110 to the medical resources allocation device 140. For example, the at least one storage device may be a built-in or backend server connected exclusively to one medical resource provider 110 and may provide medical resource information of the only medical resource provider 110. As another example, the at least one server may be shared by a plurality of medical resource providers 110 and may provide medical resource information of the plurality of medical resource providers 110.

The network 120 may include any suitable network that can facilitate the exchange of information and/or data for the allocation system. In some embodiments, one or more components of the allocation system (e.g., the medical resources provider 110, the terminal device 130, the medical resources allocation device 140, the storage 150) may communicate information and/or data with one or more other components of the allocation system via the network 120. For example, the medical resources allocation device 140 may obtain information of the medical resources from the medical resources provider 110 (as well as the medical resources providers 111, 112 and 113) via the network 120. As another example, the medical resources allocation device 140 may obtain user instructions from the terminal device 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the allocation system may be connected to the network 120 to exchange data and/or information.

The terminal(s) 130 may be or may include a mobile computing device such as a mobile device 131, a tablet computer 132, a laptop computer 133, a desktop computer (not shown), a console (not shown), or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the medical resources allocation device 140.

The terminal device 130 may include means for inputting information (e.g., keyboard, mouse, microphone, touchscreen, camera, sensor, joystick, USB port, network interface card, card reader) and/or outputting information (e.g., display, USB port, network interface card). The information may include, e.g., information related to medical resources or information related to a medical process of a patient. The information may be inputted by, e.g., the user 135 through the terminal device 130. Alternatively or additionally, the information may be obtained from the storage 150, the medical resources allocation device 140, or the medical resources provider 110 through, e.g., the network 120. The information may be transmitted to the medical resources allocation device 140 for processing, be stored in the storage 150, or be presented to the user 135 through the terminal device 130.

In some embodiments, the terminal device 130 may further include an interface for facilitating the interaction with the user 135. The terminal device 130 may display (or use any other proper means) information to the user 135 through the interface or receive inputs from the user 135 via the interface.

In some embodiments, the terminal device 130 may further include a positioning module for determining the current location of the terminal device 130. The positioning module of the terminal device 130 may communicate with a positioning system (not shown). The positioning system may determine positioning information associated with the location and/or movement of the terminal device 130. In some embodiments, the positioning system may be a global positioning system (GPS), a global navigation satellite system (GLONASS), a compass navigation system (COMPASS), a BeiDou navigation satellite system, a Galileo positioning system, a quasi-zenith satellite system (QZSS), an indoor positioning system (e.g., based on WI-FI, Bluetooth™, radio frequency identification (RFID)), etc. The positioning information may include a location, an elevation, a velocity, or an acceleration of the terminal device 130, or the current time. The location may be in the form of coordinates, such as, latitude coordinate and longitude coordinate, etc. The positioning system may send the positioning information mentioned to the positioning module of the terminal device 130 via wireless connections such as the network 120.

The medical resources allocation device 140 may allocate medical resources based on information obtained from the medical resources provider 110 (as well as the medical resources providers 111, 112, and/or 113), from a user 135 via the terminal device 130, from the storage 150, or the like, or a combination thereof. For example, the medical resources allocation device 140 may acquire information on the medical process corresponding to the user 135, and allocate medical resources for the medical process. The medical resources allocation device 140 may also notify the user 135 (e.g., through the terminal device 130) with the information on the medical process and allocated medical resources in a designated manner.

In some embodiments, the medical resources allocation device 140 may detect a medical plan arrangement application executing on the terminal device 130 of the user 135. Via the medical plan arrangement application, the user 135 may manage a medical process, such as initiating the medical resources allocation process. The notification of the medical process and allocated medical resources may also be performed via the medical plan arrangement application. After being launched, the medical plan arrangement application may automatically communicate with the medical resources allocation device 140 via the network 120.

In some embodiments, the medical resources allocation device 140 may track the location of the user 135 (or the location of the terminal device 130) via the positioning model of the terminal device 130. The medical resources allocation device 140 may allocate the medical resources based at least on the location of the user 135. Alternatively or additionally, the medical resources allocation device 140 may determine a route for guiding the user 135 from his/her current location to an allocated medical resource of a sub-process of the medical process. The sub-process may be an upcoming sub-process (i.e., the next sub-process of the medical process the user 135 is to attend) or a sub-process designated by the user 135 via the terminal device 130 (or the medical plan arrangement application). The determined route may be displayed on the display of the terminal device 130 (e.g., via an interface generated by the medical plan arrangement application).

Figure 10:
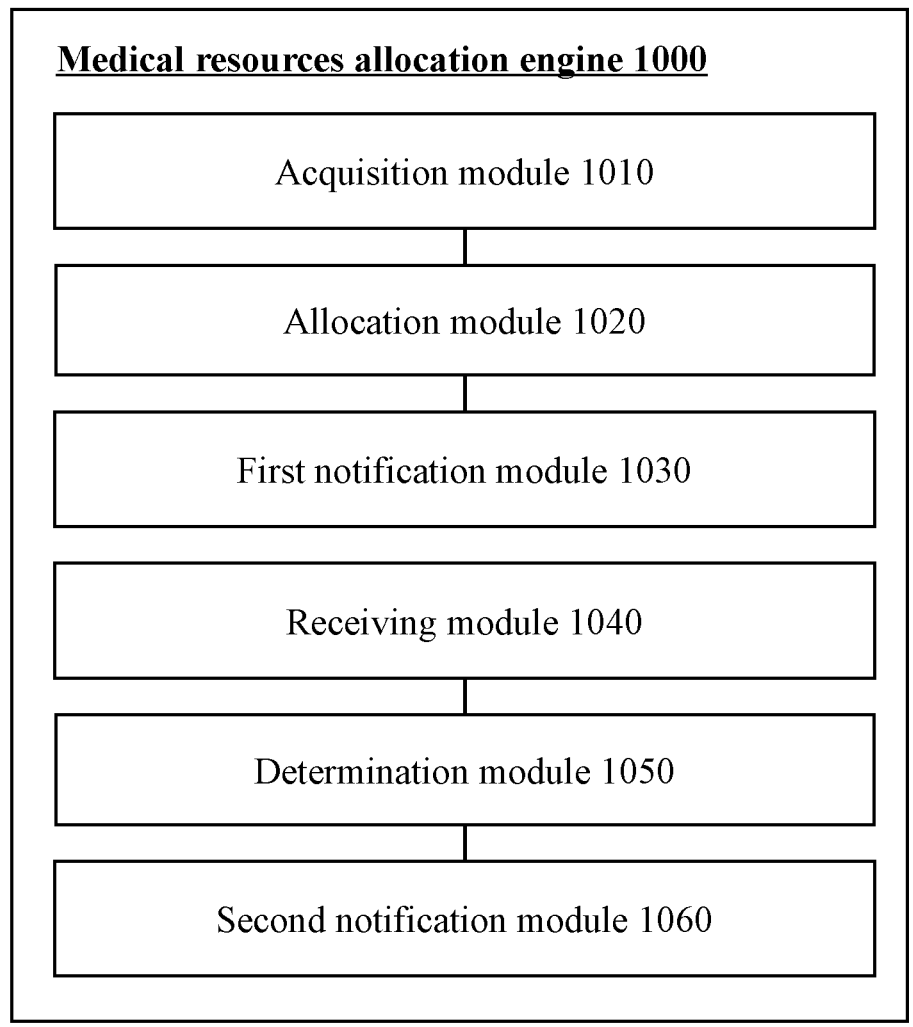
FIG. 10 is a schematic diagram illustrating an exemplary medical resources allocation device according to some embodiments of the present disclosure.

More description of the medical resources allocation device 140 may be found elsewhere in the present disclosure (e.g., in connection with FIGS. 3 and 10).

In some embodiments, the medical resources allocation device 140 may be implemented on a computer, a user console, a single server, or a server group, etc. The server group may be centralized or distributed. In some embodiments, the medical resources allocation device 140 may be local or remote with respect to the medical resources provider 110 that the medical resources allocation device 140 manages. For example, the medical resources allocation device 140 may access, via the network 120, information and/or data stored in the medical resources provider 110, provided by a user 135 via the terminal device 130, and/or the storage 150. As another example, the medical resources allocation device 140 may be at the backend of and directly connected to the medical resources provider 110, and may access information of the medical resources provider 110, including information provided by a user 135 via the terminal device 130 and/or information stored in the storage 150. In some embodiments, the medical resources allocation device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the medical resources allocation device 140 may be implemented by a computing device 200 having one or more components as illustrated in FIG. 2-A.

The storage 150 may store data, instructions, and/or any other information. In some embodiments, the storage 150 may store data obtained from the terminal device 130 and/or the medical resources allocation device 140. In some embodiments, the storage 150 may store data and/or instructions that the medical resources allocation device 140 may execute or use to perform exemplary methods described in the present disclosure. In some embodiments, the storage 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the allocation system (e.g., the medical resources allocation device 140, the terminal device 130). One or more components in the allocation system may access the data or instructions stored in the storage 150 via the network 120. In some embodiments, the storage 150 may be at the backend of and directly connected to or communicate with one or more other components in the allocation system (e.g., the medical resources allocation device 140, the terminal device 130). In some embodiments, the storage 150 may be part of the medical resources allocation device 140.

It may be noted that, FIGS. 1-A and 1-B are only provided for demonstration purposes, and is not intended to apply a limitation to the present disclosure. Modification and amendment may be made to FIGS. 1-A and 1-B. The numbers, appearances, and relative locations of the components of the allocation system (e.g., allocation system 100A or 100B) are also for illustration purposes and may not reflect their true states in practical use.

FIG. 2-A is a schematic diagram illustrating exemplary hardware and/or software components of an exemplary computing device. As illustrated in FIG. 2-A, the computing device 200 may include a processor 210, a storage 220, and an input/output interface 230.

The processor 210 may execute computer instructions (e.g., program code) and perform functions of the medical resources allocation device 140 in accordance with techniques described herein. The computer instructions may include, for example, routines, programs, objects, components, data structures, procedures, modules, and functions, which perform particular functions described herein. For example, the processor 210 may be configured to perform the functions related to the processing of the information provided by the medical resources provider(s). The processor 210 may also be configured to perform the functions related to the notifying a user (e.g., user 135) with the information.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus steps and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminal device 130, the storage 150, and/or any other component of the imaging system. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the medical resources allocation device 140 for determining a regularization item.

The input/output interface 230 may input and/or output signals, data, information, etc. In some embodiments, the input/output interface 230 may enable a user interaction with the medical resources allocation device 140. In some embodiments, the input/output interface 230 may communicate with or include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The input/output interface 230 may also be connected to a network (e.g., the network 120) to facilitate data communications. The input/output interface 230 may establish connections between the medical resources allocation device 140 and the medical resources provider 110 (as well as the medical resources providers 111, 112, and 113), the terminal device 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or a combination thereof. In some embodiments, the input/output interface 230 may be and/or include a standardized communication port, such as RS232, RS485, etc. In some embodiments, the input/output interface 230 may be a specially designed communication port. For example, the input/output interface 230 may be designed in accordance with the digital imaging and communications in medicine (DICOM) protocol.

FIG. 2-B is a schematic diagram illustrating exemplary hardware and/or software components of an exemplary mobile computing device. As illustrated in FIG. 2-B, the mobile device 250 may include a communication platform 260, a display 270, a graphic processing unit (GPU) 271, a processor 272, an I/O 273, a memory 280, and a storage 275. In some embodiments, any other suitable component, including but not limited to a system bus or a controller (not shown), may also be included in the mobile device 250. In some embodiments, a mobile operating system 281 (e.g., iOS™, Android™, Windows Phone™) and one or more applications 282 may be loaded into the memory 280 from the storage 275 in order to be executed by the processor 272. User interactions with the information stream may be achieved via the I/O 273 and provided to the medical resources allocation device 140 and/or other components of the imaging system via the network 120.

The applications 282 may include a browser or any other suitable mobile apps for receiving and/or rendering information related to the allocation of medical resources of the medical resources provider 110 from the medical resources allocation device 140. The application 282 may also include any other suitable mobile apps for inputting information (e.g., requests) and/or facilitate an interaction between a user 135 and the medical resources allocation device 140.

In the present disclosure, the application 282 may also be referred to as a medical plan arrangement application. The application 282 may receive data (encrypted or not encrypted) from the medical resources allocation device 140 via the network 120. In response to the received data, the application 282 may generate a presentation (e.g., in the form of a user interface or an element or feature of a user interface), and display information included in the received data. In some embodiments, the application 282 may provide user interface features for the user 135 to trigger transmission of a request (encrypted or not encrypted) to the medical resources allocation device 140. The request may initiate a corresponding function or process by the medical resources allocation device 140.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

FIG. 3 is a schematic diagram illustrating an exemplary medical resources allocation device according to some embodiments of the present disclosure. The medical resources allocation device 140 may include an acquisition module 310, an allocation module 320, and a first notification module 330.

The acquisition module 310 may be configured to acquire information on the medical process (first information) related to the user 135 (e.g., a patient).

The medical process may include a plurality of sub-processes such as creating the medical records or the user profile, first visit, examination, second visit, treatment, follow-up examination, post treatment monitoring, etc. Each sub-process may relate to one or more medical services or medical resources provided by the medical resources provider(s). The first information may include information on the medical process and the sub-processes thereof.

In some embodiments, the acquisition module 320 may identify sub-processes of the medical process based on the first information. The first information may include, for example, a list of the sub-processes of the medical process, a sequece of the sub-processes, a time slot for attending a sub-process (e.g., check-in time, appointment time, an estimated duration of a sub-process), the place of the visit of a sub-process, or the like, or a combination thereof.

In some embodiments, the first information may include time information for one or more sub-processes. For example, a sub-process may be associated with time information including a time slot (or be referred to as schedule time slot) during which the user 135 intends to or is arranged to attend the sub-process. The allocation of medical resource for such a sub-process may be performed according to the associated time information.

The first information may be determined based on, for example, a designated doctor or therapist for the user 135, the preference of the user 135, information related to one or more medical resources providers (e.g., a list), or the like, or a combination thereof. The medical process may be determined as a whole (e.g., for a routine health examination), determined sub-process by sub-process (e.g., for diagnosing and/or treating a disease), determined in a batch of sub-processes (e.g., for a treatment plan including a series of sub-processes), etc. In some embodiments, a sub-process or a batch of sub-processes may be determined based on the result(s) of one or more previous sub-processes.

The first information may be determined and inputted into the medical resources allocation device 140 by a user 135 (e.g., a designated doctor, a designated nurse, an assistant who may assist in making appointments, and/or the patient). Alternatively or additionally, the first information may be determined and inputted into the medical resources allocation system 100A or 100B by a medical used intelligent device (not shown in FIGS. 1-A and 1-B). For example, the intelligent device may acquire information on symptoms of a user 135 (e.g., a patient). The information on symptoms may be inputted by the user 135 through a terminal device 130 and/or collected by an information acquisition device (e.g., one or more electrodes, a camera). The intelligent device may determine the first information by matching the information on symptoms and a plurality of pre-stored medical process template associated with different symptoms. Alternatively or additionally, the intelligent device may provide a plurality of medical-process options for a user 135 (e.g., a doctor or technician) to choose from, and determine the first information based on a choosing result.

The determined first information may be stored in a first storage device (e.g., the storage 150, the storage 220, the storage 275, the memory 280) of the medical resources allocation system 100A or 100B. The acquisition module 310 may acquire the first information from the first storage device through, e.g., the network 120.

The allocation module 320 may be configured to allocate available medical resources for the medical process specified in the first information. An "available medical resource" may refer to a medical resource that the medical resources allocation device 140 can allocate to a user (e.g., the user 135) and may not necessarily indicate or imply that the medical resource is currently idle or in stock. For simplicity, unless otherwise noted, the medical resources referred to in the present disclosure are or "available medical resources" for the medical resources allocation device 140 or embodiments thereof.

The allocation module 320 may allocate medical resources based on the first information and information on available medical resources (second information). The second information may include available time slots (or idle time slots) of the corresponding medical resources. The allocation module 320 may identify available medical resources based on the first information and the second information, and then perform the allocation of the medical resources for the medical process according to the first information.

The second information may be stored in a second storage device (e.g., the storage 150, the storage 220, the storage 275, the memory 280) providing medical resource information of one or more medical resource providers. The allocation module 320 may obtain the second information from the second storage device through, e.g., the network 120. The second information may be provided and maintained by the one or more medical resources providers. The second information may be updated periodically or in real-time by the one or more medical resources providers.

The first storage device for storing first information and the second storage device for storing the second information may be the same storage device or different storage devices. The first storage device and/or the second storage device may be remote or local. In some embodiments, the first storage device and/or the second storage device may be included in the medical resources allocation device 140.

In some embodiments, to allocate the medical resources for the medical process, for each sub-process of the medical process, the allocation module 320 may determine, based at least on the first information, a schedule time slot of the sub-process. The allocation module 320 may then determine, from the medical resources, based on the first information and second information, one or more candidate medical resources that satisfy a criterion of being available during the schedule time slot of the sub-process. The allocation module 320 may select a target medical resource from the one or more candidate medical resources, and assign the target medical resource to the sub-process as the allocated medical resource of the sub-process.

The first notification module 330 may notify the user 135 with the first information and the allocated medical resources in a designated manner.

After the allocation of the medical resources for the medical process, the first notification module 330 may determine, for one or more sub-processes of the plurality of sub-processes, appointment information of the one or more sub-processes based on at least a portion of the second information corresponding to the medical resource allocated to the one or more sub-processes. The appointment information of a sub-process may include information on the allocated medical resource of the sub-process, and may be for presentation on a user interface of the terminal device 130 (e.g., generated or provided by the aforementioned medical process arrangement application). For example, the appointment information may include a time point or time slot for a patient to access the allocated medical resource of the sub-process and/or for a doctor/technician to provide the allocated medical resource to the patient. In some embodiments, the appointment information may further include a location for a patient to access the allocated medical resource.

In some embodiments, the appointment information of a sub-process may further include other information on the allocated medical resource or a link to such information. For example, the appointment information may include an introduction of the medical resource (e.g., medical equipment, medicine, attending doctor).

In some embodiments, the appointment information of a sub-process may further include information on the sub-process or a link to such information. For example, the appointment information may include an introduction of the sub-process or a link to it.

The notification manner may be designated by a user 135 or the first notification module 330 itself. For example, the first notification module 330 may provide (e.g., through an interface of the terminal device 130) different notifying manners to be selected through the terminal device 130 and receive instructions related to the selection of the notification manner from the operator. Different users 135 related to a same medical process for a same patient may designate different notification manners regarding the same medical process.

In some embodiments, the first notification module 330 may notify a user 135 with the appointment information of at least one sub-process of the plurality of sub-processes of the medical resources specified in the first information.

The medical resource allocation device 140 may be configured to perform medical resource allocation processes described in the present disclosure (e.g., processes 400, 500, 700, and 900 illustrated in FIGS. 4, 5, 7, and 9). More descriptions of the medical resource allocation device 140 and the modules thereof may be found elsewhere in the present disclosure.

It may be noted that, the above description about medical resources allocation device 140 is only for illustration purposes, and is not intended to limit the present disclosure. It is understandable that, after learning the major concept and the mechanism of the present disclosure, a person of ordinary skill in the art may alter medical resources allocation device 140 in an uncreative manner. The alteration may include combining and/or splitting modules or sub-modules, adding or removing optional modules or sub-modules, etc. All such modifications are within the protection scope of the present disclosure.

Figure 4:
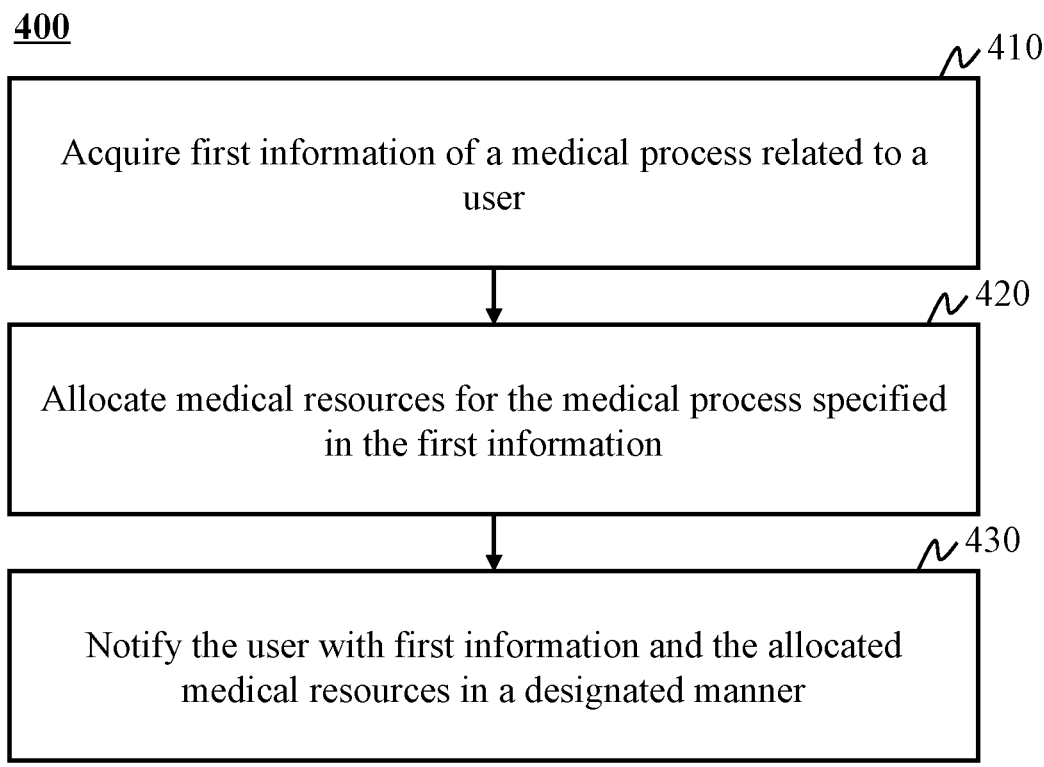
FIG. 4 is a schematic diagram illustrating an exemplary process for the medical resources allocation according to some embodiments of the present disclosure.

FIG. 4 is a schematic diagram illustrating an exemplary process for the medical resources allocation according to some embodiments of the present disclosure. Process 400 may be performed by the medical resources allocation device 140 for allocating medical resources of one or more medical resources providers (e.g., medical resources providers 110~113) for a medical process of a user (e.g., user 135). In some embodiments, one or more operations of process 400 illustrated in FIG. 4 for medical resources allocation may be implemented in the medical resources allocation system illustrated in FIGS. 1-A and 1-B. For example, the process 400 illustrated in FIG. 4 may be stored in the storage 150 in the form of instructions, and invoked and/or executed by the medical resources allocation device 140 (e.g., the processor 210 of the computing device 200 as illustrated in FIG. 2-A). One or more operations of the process 400 may be executed by one or more sub-modules of the medical resources allocation device 140.

In 410, the acquisition module 310 may acquire first information of a medical process related to the user 135 (the first information as described in connection with FIG. 3). The acquisition module 310 may acquire the first information from a storage device (e.g., storage 150) of the medical resources allocation system 100A or 100B through the network 120.

In some embodiments, a user 135, e.g., a doctor or nurse designated for a patient or an assistant using the medical resources allocation system 100A or 100B, may determine the medical process for the user 135 and input the related information into the medical resources allocation device 140 through a terminal (e.g., the terminal device 130). Optionally, on the terminal, an interface may be provided for presenting and/or receiving the first information to/from the user 135. The doctor, the nurse, or the assistant may input the needed information according to, e.g., a prompt (e.g., in the form of a textbox, a checkbox, a menu) indicating a sub-process to be operated on the interface of the terminal.

In some embodiments, the medical resource allocation system 100A or 100B may include an intelligent device (or module) for automatically determining the medical process for the user 135 and input the related information into the medical resources allocation device 110. The intelligent device may determine the medical process based on one or more standard templates. Alternatively or additionally, the intelligent device may determine the medical process based on identity information of the user 135, biological information (e.g., finger prints, facial features) of the user 135, medical records (e.g., including one or more previous examination results) of the user 135, symptom description (e.g., in the form of voice, image, text) of the user 135, or the like, or a combination thereof.

In some embodiments, the first information may be further maintained or altered by a user 135 (e.g., by a designated doctor, a designated nurse, an assistant) or the intelligent device during the medical process of the patient. For example, after an examination sub-process of the process, additional examination sub-process or a therapy or treatment sub-process may be added (e.g., by the doctor, the nurse, the assistant) or the intelligent device into the medical process based on the result of the examination sub-process.

In some embodiments, the first information may include at least some of the plurality of sub-processes (first time information). For example, during the determination of the medical process, a user 135 (e.g., a doctor, a nurse, an assistant) or the intelligent device (e.g., a mobile computing device) may add an appointment time (a time slot including the start time and/or an end time) for one or more sub-processes without considering the available medical resources (e.g., for the convenience of the user 135). Alternatively or additionally, the schedule time slot of one or more sub-processes may be determined based on available medical resources in 420. As used herein, a time slot may include only a start time, only a time duration, or a start time and an end time, or the like, or a combination thereof.

In some embodiments, a user 135 (e.g., a doctor, a nurse, an assistant) or the intelligent device may assign a priority factor to a medical process or a portion thereof (e.g., a sub-process of the medical process) such that the timing of the medical process or a portion thereof may be arranged accordingly, and the time information may be determined accordingly. For instance, for a patient user 135 with an urgent condition, his medical process or a portion thereof may be assigned a high priority factor such that his medical process or a portion thereof may be arranged with higher priority than pre-existing medical process(es) for one or more other patient users 135 with less urgent condition(s). The medical resources allocation device 110 may determine time information for the patient user 135 with the urgent condition accordingly.

In 420, the allocation module 320 may allocate medical resources for the medical process specified in the first information. The allocation may be performed based on the first information and information on available medical resources (second information).

In some embodiments, the allocation module 320 may obtain the second information from, e.g., the medical resources allocation device 110 or a portion thereof (e.g., at least one storage device belonging to or connected with the medical resources allocation device 110). Alternatively or additionally, the allocation module 320 may obtain the second information, via the network 120 from at least one storage (e.g., the storage 150) accessible to the network 120. Based on the first information, the allocation module 320 may identify sub-processes of the medical process to allocate the medical resources. Based on the second information, the allocation model may determine or select one or more candidate medical resources from a plurality of medical resources of one or more medical service providers for each sub-processes of the medical process.

In some embodiments, for a sub-process of the medical process, the allocation module 320 may aquire the second information associated with the sub-process based on the first information of the sub-process (e.g., the type/name of the medical process, the type/name of the sub-processes(s)). For example, for a sub-process including a CT examination, the allocation module 320 may acquire the information on CT related medical resources (e.g., the available hours of doctors or the technicians, the status of the medical devices (e.g., occupied, reserved for one or more specific time slots, information regarding the reservation(s) (e.g., the purposes of the reservations, the conditions of the patients for which the reservations are made), scheduled for maintenance or repair), the location of the medical resources) and store the information into a storage device before the allocation.

In some embodiments, the information acquisition of second information associated with a variety of sub-processes or medical processes may be performed periodically (e.g., every one or more minutes, every one or more hours, every one or more days). Alternatively or additionally, the information acquisition may be performed in response to an instruction of a user 135 (e.g., a doctor, a nurse, an assistant, a patient) or the intelligent device to initialize the allocation operation with respect to a medical process.

In some embodiments, the allocation module 320 may perform or initiate a medical resource allocation process by programmatically executing, for each sub-process of the medical process (or for each sub-process of at least some of the sub-processes of the medical process), a process as following. First, the allocation module 320 may determine, based at least on the first information of the sub-process, a schedule time slot of the sub-process for allocating one or more corresponding medical resources. The allocation module 320 may then search for medical resources satisfying one or more criteria of being available during the schedule time slot of the sub-process based at least on the second information. The medical resource(s) included in the search result may be referred to as candidate medical resource(s). For example, a candidate medical resource may have one or more available time slots within the schedule time slot of the sub-process. An available time slot may be a time slot supposed to be sufficient to perform the corresponding sub-process during which the corresponding medical resource is not occupied by a user (e.g., a patient). The allocation module 320 may determine (or select) a target medical resource (or a set of target medical resources) from the found candidate medical resource(s) using an algorithm or in response to an instruction of a user 135. The allocation module 320 may then assign the target medical resource to the sub-process to achieve the medical resource allocation of the sub-process. When only one candidate medical resource (or one set of medical resources) is found by the allocation module 320, the selection of the medical resource may be skipped.

In some embodiments, to assign a medical resource (e.g., the target medical resource) to a sub-process of the user 135, the allocation module 320 may modify or update the second information corresponding to the medical resource in the second storage device, so that the time slot corresponding to the medical resource may be labeled as occupied in the second information and the medical resource cannot be allocate to another sub-process or another user.

In some embodiments, the allocation module 320 may perform the searching based on one or more additional criterion, such as a location range (e.g., the city, the district), a grade range of the corresponding service, etc. For example, a user A may arrange his/her medical process according to his/her business plan, and may decide to attend a sub-process A of the medical process in a city A during a time period A and attend a sub-process B of the medical process in a city B during a time period B. Data representing such a medical process arrangement may be included in the first information of the user A. When allocating a medical resource for the sub-process A, based on the first information of the user A, the allocation module 320 may set the schedule period of the sub-process A as the time period A, set the search criterion to include criterion such as "being available during the time period A" and "in the city A", and assign a founded candidate medical resource to the sub-process A. Similar process may be performed by the allocation module 320 to allocate a medical resource for the sub-process B.

The allocation module 320 may automatically or programmatically select a target medical resource for a sub-process to fulfill the need of one or more users 135 (e.g., a patient, a doctor, a nurse, and/or an assistant) based on one or more criterion. Alternatively or additionally, the allocation module 320 may present the information on the candidate medical resources of a sub-processes to one or more users 135 (e.g., the patient, the doctor, the nurse, and/or the assistant). The One or more users 135 may make manually select, via the terminal device 130 (or the medical plan arrangement application), a target medical resource from the candidate medical resources for the sub-processes according to the information presented. In response to the selection made by the one or more users 135, the allocation module 320 may assign the target medical resource to the sub-process. Detailed information of the manual selection may be found elsewhere in the present disclosure (e.g., in connection with FIG. 9).

In some embodiments, the allocation module 320 may automatically or programmatically select a target medical resource from a plurality of candidate medical resources based on the costs of the candidate medical resources. The allocation module 320 may determine the cost of a candidate medical resource based on, for example, factors including the time cost (e.g., the waiting time to the start time point of the available time slot of the candidate medical resource), the financial cost (e.g., a fee for the usage of the medical resource), the travel cost (e.g., e.g., a distance from a location (e.g., home, work place, the current location, a location where the previous sub-process is attended) designated by the user to the candidate medical resource), or the like, or a combination thereof. The allocation module 320 may select a candidate medical resource, for example, with the minimum cost as the target medical resource.

In some embodiments, the schedule time slots of one or more sub-processes may be included in the first information. For example, the schedule time slots may be designated by a user 135 during the determination or generation of the first information.

In some embodiments, the allocation module 320 may select a target medical resources based further on the locations of the medical resources. For example, the allocation module 320 may determine a location associated with the user 135 for the current sub-process. The location may be the current location of the user 135, the home of the user 135, the workplace of the user 135, a room rent by the user 135, the location where the previous sub-process is to be attended by the user 135, etc. The allocation module 320 may determine the locations of the medical resources (e.g., candidate medical resources) associated with the current sub-process based on the second information, and determine distances from the location associated with the user 135 to the medical resources. The allocation module 320 may then allocate the medical resources based on the determined distances. For example, a plurality of medical resources being available during the schedule time slot of a sub-process may be determined as candidate medical resources. The allocation module 320 may select a medical resource, for example, having a minimum distance as the target medical resource. The allocation module 320 may also display information on the plurality of medical resource providers or the plurality of medical resources through the terminal device 130 for the user 135 to choose from.

After a sub-process of the medical process is assigned or allocated a medical resource (or a set of medical resources), the allocation module 320 may designate the time slot corresponding to the medical resource as the time slot (or be referred to as attendance time slot) for the user 135 to attend the sub-process. The attendance time slot may be the same as or different form the schedule time slot. For example, the schedule time slot of a sub-process may be 9:00 am to 11:00 am for a sub-process A. But during the schedule time slot, an earliest available time slot of the assigned medical resource of the sub-process A may be 9:30 am to 10:00 am. The attendance time slot may then be determined as 9:30 to 10:30.

In some embodiments, the first information may include a sequence of at least some of the sub-processes of the medical process without time information associated with the sub-processes. The allocation of medical resources may be performed sequentially in accordance with the sequence of the sub-processes. For the first sub-process of the sub-processes, the allocation module 320 may search for a corresponding medical resource with an available time slot closest to the current time (the time when the allocation is executed). For example, the allocation module 320 may set the schedule time slot of the first sub-process as starting from the current time with a proper time period (e.g., 3 days, a week, a month). By allocating a searched medical resource to the first sub-process, the attendance time slot of the first sub-process may be determined or arranged as the closest available time slot of the allocated medical resource. Similarly, for a subsequent sub-process of the sub-processes, the allocation module 320 may search (automatically or semi-automatically) for a medical resource with an available time slot closest to the attendance time slot of the sub-process previous to the sub-process of interest, and allocating the searched medical resource to the sub-process of interest. For example, the allocation module 320 may set the schedule time slot of the sub-process as starting from the supposed ending time point of the previous sub-process (e.g., the ending time point of the attendance time slot of the previous sub-process) with a proper time period. The attendance time slot of the subsequent sub-process may be determined or arranged as the earliest or closest available time slot of the allocated medical resource.

In some embodiments, some of the sub-processes of the medical process may not have to be sequentially attended (e.g., different physical tests or examinations for the diagnosis). The allocation module 320 may set a common schedule time slot for such sub-process as starting from the supposed ending time point of the sub-process have to be attended previous to these sub-processes (e.g., the first visit) with a proper time period (e.g., 3 days, a week, a month). The sequence of the sub-processes may be determined based at least on the time sequence of the available time slots (or the start time point thereof) of the medical resources associated with these sub-processes. In some embodiments, the determined sequence of the sub-processes may satisfy that one or more key sub-processes of the sub-processes is to be allocated with corresponding medical resources with earliest start time points of the available time slots.

The search of medical resources may be performed based further on one or more other search criteria. For example, the search criteria may include a location range (e.g., the city, the district), a grade range of the corresponding service, etc.

After the allocation of medical resource is completed, the allocation module 320 may generate, for each sub-process of the plurality of sub-processes, the appointment information of the sub-process based on information associated with the allocated medical resource of the sub-process (e.g., retrieved from the second information) and information associated with the sub-process (e.g., retrieved from the first information). In some embodiments, the appointment information may include a determined attendance time slot for each sub-process or the medical process.

It may be noted that, in some embodiments, the medical process may include one or more sub-processes (e.g., registration, payment) required no medical resources or don't have to be allocated with corresponding medical resources (e.g., the corresponding medical resources are expected to be always available). The allocation module 320 may skip the medical resource allocation for such a sub-process. For convenience, unless otherwise noted, the "sub-processes" referred to in the present disclosure are all sub-processes to be allocated with medical resources.

In some embodiments, the allocation module 320 may perform the allocation of medical resources for a medical process based on a rulebook, information of the medical process (first information) and information of the medical resources (second information). The rulebook may include rules for allocating medical resources.

For instance, The rulebook may include one or more rules for determining available time slots of the medical resources based on the second information regarding the medical resources such as needed warm-up time of a medical device (e.g., an imaging machine, a treatment apparatus), needed cool-down time of a medical device between consecutive uses or before shut-down, a maximum operation time of a medical device within a period of time (e.g., a day, a week), needed calibration time or maintenance time of a medical device, scheduled calibration or maintenance to be performed on a medical device, a maximum period of time a same operator can continuously work on a medical device without taking a break, one or more conditions to be checked before a patient can be operated on a medical device or a medical procedure, or the like, or a combination thereof.

For instance, the rulebook may include one or more rules for determining schedule time slot of a sub-process based on at least a portion of the first information, such as time information of the sub-process (if any), time information of the previous sub-process (if any), the sequence of the sub-processes of the medical process, or the like, or a combination thereof.

For instance, the rulebook may include one or more rules corresponding to one or more of the searching criterion for searching for candidate medical resources described in the present disclosure or any other searching manners in the art.

For instance, the rulebook may include one or more rules corresponding to one or more of the aforementioned target medical resource selecting manners described in the present disclosure or any other selecting manners in the art.

In some embodiments, during the operation 420, the allocation module 320 may adjust or change rules for allocating the medical resource from the rules in the rulebook. For example, the allocation module 320 may initially retrieve (or select) a first rule (or a set of first rules) from the rulebook for performing an operation of the allocation of resources for the medical process. When the allocation module 320 fails to allocate medical resources for a sub-process of the medical process based on the first set of rules (e.g., fails to find candidate medical resources, fails to select a target medical resource, fails to determine available time slots of corresponding medical resources, fails to determine a schedule time slot of the sub-process), the allocation module 320 may programmatically adjust the first rule(s) or retrieve (or select) a second rule (or a set of second rules) from the rulebook. The allocation module 320 may then continue to allocate the medical resources for the sub-process based at least one the second rule(s). For example, the allocation module 320 may continue to allocate the medical resources for the sub-process based solely on the second rule(s). As another example, the allocation module 320 may continue to allocate the medical resources for the sub-process based on at least one of the first rule(s) and the second rule(s). The allocation of medical resources for the next sub-process in the medical process may be performed initially still based on the first rule(s). Alternatively or additionally, the allocation of medical resources for the next sub-process in the medical process may be performed initially based on the second rule(s), or based on at least one of the first rule(s) and the second rule(s).

The rulebook may be maintained and updated periodically or when a relevant update becomes available.

In 430, the first notification module 330 may notify the user 350 with the first information and the allocated medical resources in a designated manner. The notification manner may be designated by a user 135 (e.g., the patient, a doctor or nurse of the patient, an assistant who may use the medical resources allocation device 140 to arrange the medical process), or the first notification module 330 itself. The first notification module 330 may notify the user 135 programmatically or in response to an instruction of the user 135.

In some embodiments, different users 135 related to a same medical process for a same patient may designate different notification manners regarding the same medical process. The contents sent to different users 135 related to the same medical process may be the same or different. For instance, the patient may receive information regarding the time, the location, and the preparation on the side of the patient in a manner designated by the patient, and the doctor or the nurse may receive at least part of the information mentioned above that the patient receives, as well as the preparation on the side of the doctor or the nurse, etc., in a manner designated by the doctor, the nurse, or the medical resources allocation device 140.

In some embodiments, the first notification module 330 may determine, for at least one sub-processes of the plurality of sub-processes to be informed or notified, appointment information of the at least one sub-process based on at least a portion of the second information corresponding to the medical resource allocated to the at least one sub-process. The appointment information of a sub-process may include information on the allocated medical resource of the sub-process. For example, the information on the allocated medical resource may include information on the location and attendance time slot of the allocated medical resource. The first notification module 330 may then notify the user 135 with the appointment information of the at least one sub-process. In some embodiments, the information on the attendance time slot of a sub-process may include the start time point of the attendance time slot.

In some embodiments, to notify the user 135, the first notification module 330 may provide first data corresponding to the appointment information of the at least one sub-process to be sent to the terminal device 130 of the user to generate a first presentation on the display of the terminal device 130. For example, the first data may be received by the medical plan arrangement application executing on the terminal device 130, and which may generate the first presentation in response to the first data. The first presentation may be, for example, a webpage, a user interface, a pushed information, an email, a short messaging service (SMS), an instant message, etc. The first presentation may include the appointment information of the at least one sub-process. The medical resources allocation device 140 may transmit the first data to the terminal device 130 through the network 120. As another example, the first notification module 330 may notify a user 135 with the appointment information via a voice message or a telephone call.

In some embodiments, the first notification module 330 may encrypt the first data and provide the encrypted first data to the terminal device 130 (or the medical plan arrangement application) for generating the first presentation, so as to protect the privacy of the user 135.

A user 135 may designate or select the manner of the notification. For example, via a user interface provided by a medial plan arrangement application or software executing on a terminal device 130 of the user 135, the medial plan arrangement application may generate and transmit a notification designation request for designating or selecting a manner of the notification to the medical resources allocation device 140 via the network 120. After receiving the notification designation request, the server 130 may determine the notification manner based on the notification designation request and initiate a corresponding notification process when one or more sub-processes of the user 135 are to be notified.

In some embodiments, the first notification module 330 may notify a user 135 with the appointment information of some of or all of the sub-processes of the medical process. The first presentation may include an overview (or a list) of the sub-processes to be notified and a corresponding allocated medical resource (or a set of allocated medical resources) displayed besides each corresponding sub-process of the sub-processes to be notified. In some embodiments, the first presentation may further include a corresponding attendance time slot displayer besides each corresponding sub-process.

In some embodiments, the first notification module 330 may notify a user 135 with the appointment information of an upcoming sub-process (the next sub-process to be attended by the user) of the medical process. The upcoming sub-process may be a sub-process has an attendance time slot (or the start time point of the attendance time slot) closest to the current time after the current sub-process (or current progress) of the medical process. The first notification module 330 may determine or identify the upcoming sub-process based on the first information. Alternatively or additionally, the first notification module 330 may determine or identify the upcoming sub-process based on the attendance time slots (or the start time point thereof) of at least some of the subsequent sub-processes (e.g., when the first information lacks the sequence information on some sub-processes).

In some embodiments, the first notification module 330 may determine a notification time point for notifying the user 135 with the appointment information of the upcoming sub-process. For example, the first notification module 330 may determine a closest time point (with respect to the current time) associated with the upcoming sub-process after the current progress of the medical process, and then determine the notification time point based on the closest time point. The closest time point may be the start time point of the attendance time slot of the upcoming sub-process, the start time point of the schedule time slot of the upcoming sub-process, etc. The notification time point may be the closest time point or a time point before the closest time point with a predetermined time interval (e.g., 15 min, 1 h, 3 h, 1 d). Alternatively or additionally, the notification time point may be the time point when the current sub-process is completed, the ending time point of the attendance time slot of the current sub-process, etc.

In some embodiments, the first notification module 330 may notify a user 135 by transmitting (e.g., pushing) the appointment information of one or more sub-processes of the medical process to a private mobile device of the user 130 via the network 120.

In some embodiments, the first notification module 330 may notify the user 135 by transmitting the appointment information of one or more sub-processes of the medical process of the user 135 to a public electronic bulletin board. The public electronic bulletin board may also be used to display appointment information of other users (concurrently or sequentially). To distinguish the appointment information of different users, the first notification module 330 may also transmit identity information of the user 135 (e.g., name, image, I.D. number, cell phone number, reservation number) with the appointment information of the user 135. The identity information may be displayed beside the appointment information on the public electronic bulletin board. To protect the privacy of the user 135, in some embodiments, the first notification module 330 may mask a part of the identity information.

In some embodiments, when the allocation module 320 determines that there are no available corresponding medical resources within the schedule time slot of a sub-process, the allocation module 320 may notify the user 135, so that the user 135 may update or modify the schedule time slot of the sub-process accordingly.

In some embodiments, the process 400 may further include a navigation process for determinining a route to guide the user 135 (e.g., a patient) to an allocated medical resource of a sub-process (e.g., the upcoming sub-process or a sub-process designated by the user 135 via the terminal device 130) of the medical process. For example, the first presentation may also provide a first user interface feature (e.g., an icon, a dialog box, a button). From the first user interface feature, the user can trigger a transmission of a navigation request (encrypted or not encrypted) to the medical resources allocation device 140 to initiate a determination of a route from the current location of the user 135 to the medical resource included in the first presentation. As another example, the medical arrangement application executing on the terminal device 130 of the user 135 may provide a navigation interface for the user 135 to input a sub-process or select a sub-process of the medical process. Via the navigation interface, the user 135 may trigger a transmission of a navigation request (encrypted or not encrypted) to the medical resources allocation device 140 to initiate a determination of a route from the current location of the user 135 (or any other location inputted by the user 135 via the navigation interface) to the medical resource allocated to the sub-process inputted or selected by the user 135.

The navigation module may determine, based on location data determined by the medical plan arrangement application executing to interface with the positioning module of the mobile computing device, the current location of the mobile computing device (or the user 135). The location data may be included in the navigation request or be retrieved by the navigation module via a separate transmission. The navigation module may also determine the location of the assigned medical resource of the sub-process based on the second information. The navigation module may then determine a route from the current location to the location of the medical resource assigned to the sub-process via a route determining algorithm in the art (e.g., a Dijkstra algorithm, an A-star algorithm). The navigation module may provide navigation data including the determined route to the terminal device 130 or the medical plan arrangement application to generate a second presentation (e.g., in the form of an interface) on the display of the terminal device 130. The second presentation may include a map. On the map, the second presentation may depict the current location of the terminal device 130, the location of the medical resource assigned to the sub-process; and the determined route.

In some embodiments, the navigation module may encrypt the navigation data and provide the encrypted navigation data to the terminal device 130 (or the medical plan arrangement application) for generating the second presentation, so as to protect the privacy of the user 135.

In some embodiments, the medical plan arrangement application may determine if the user 135, at his/her current movement rate and following the determined route, may reach the location for attending the next sub-process in time. The medical plan arrangement may alert the user 135 and/or urge the user 135 to move faster if it determines that the user 135 moves at a rate lower than a threshold and is likely to be late for the next sub-process. The threshold may be determined by the medical plan arrangement application or the medical resources allocation device 140 based on information of the user 135 (e.g., his age, his health condition), information regarding the geographic condition of the location where the user 135 currently is (e.g., a stairway, an elevator, an escalator, a hallway, a cross-walk), or the like, or a combination thereof. In some embodiments, the medical plan arrangement application may generate a signal to notify another user 135 (e.g., the doctor or the technician) that the user 135 is expected to reach the next sub-process on time or not, and/or if the user 135 needs assistance to reach the sub-process on time. In some embodiments, the mobile application may generate a signal to notify people in the vicinity of the user 135 that the user 135 is in a hurry so that the people may yield to the user 135. Such a signal may be generated by the medical plan arrangement application or by the medical resources allocation device 140 based on information provided by the medical plan arrangement application.

In some embodiments, the terminal device 130 may provide real-time positioning information of the terminal device 130, including the surrounding, to the medical resources allocation device 140 via the medical plan arrangement application. The medical resources allocation device 140 may have, e.g., a map for an area within which the user 135 moves. The map may be pre-stored in the medical resources allocation device 140 (e.g., a map of a medical resources provider), or provided by the medical plan arrangement application, or retrieved from a storage device based on an identification information provided by, e.g., the user 135 or the medical plan arrangement application. Based on the map and the real-time positioning information acquired by the terminal device 130 and provided to the medical resources allocation device 140 by the terminal device 130, the medical resources allocation device 140 may determine if a signal described above needs to be generated and generate a signal accordingly.

It may be noted that the above descriptions of the determining of the focal point are only for demonstration purposes, and not intended to limit the scope of the present disclosure. It is understandable that, after learning the major concept and the mechanism of the present disclosure, a person of ordinary skill in the art may alter process 400 in an uncreative manner. For example, the operations above may be implemented in an order different from that illustrated in FIG. 4. One or more optional operations may be added to the flowcharts. One or more operations may be divided or be combined. All such modifications are within the protection scope of the present disclosure.

For example, in some embodiments, the allocation of medical resources (the operation 420) may be performed in response to the instruction or request of the user 135. For example, the medical resources allocation device 140 may communicate with a medical plan arrangement application executing on the terminal device 130 to receive a medical resources allocation request. After receiving the medical resource allocation request, the medical resources allocation device 140 may initiate the operation 420.

In some embodiments, when communicating with the medical plan arrangement application, the medical resources allocation device 140 may provide second data regarding the medical process related to the user 135 to be sent to the medical plan arrangement application. The second data may cause the medical plan arrangement application executing on the terminal device 130 to generate a third presentation (e.g., an interface, a webpage, an SMS message, an E-mail) on the display of the mobile computing device, wherein the third presentation depicts the medical process related to the patient and provides a second user interface feature (e.g., a dialog box, one or more buttons or icons) from which the user can trigger transmission of the medical plan arrangement request (encrypted or not encrypted) to the medical resources allocation device 140.

As another example, the process 400 may not necessarily be performed for allocated medical resources for all the sub-processes of a medical process. In some embodiments, additional sub-processes may be added to the medical process of a user according to the diagnosis result or the user's response to the treatment. As a result, the medical process, as well as the corresponding first information, may be kept updated. In response to a detection that an additional sub-process is added into the medical process, the medical resources allocation device 140 may perform the process 400 to allocate medical resources for the additional sub-process. Alternatively or additionally, the medical resource allocation device 140 may perform the process 400 to allocate medical resources for one or more additional sub-processes in response to an instruction (e.g., generated and transmitted via the medical arrangement application) of a user.

In some embodiments, the medical resource allocation device 140 may allow a release of an allocated medical resource of a sub-process (e.g., a sub-process to be removed from the medical process or to be re-allocated with medical resources). To release an allocated medical resource, the medical resource allocation device 140 may modify or update second information corresponding to the medical resource to be released in the second storage device, so that the time slot corresponding to the medical resource may be labeled as unoccupied in the second information and the medical resource can be allocated by the medical resource allocation device 140 again.

In some embodiments, a medical process of a user may only include one sub-process to be allocated with medical resources, the medical resources allocation device 140 may also perform the process 400 for such a medical process.

Figure 5:
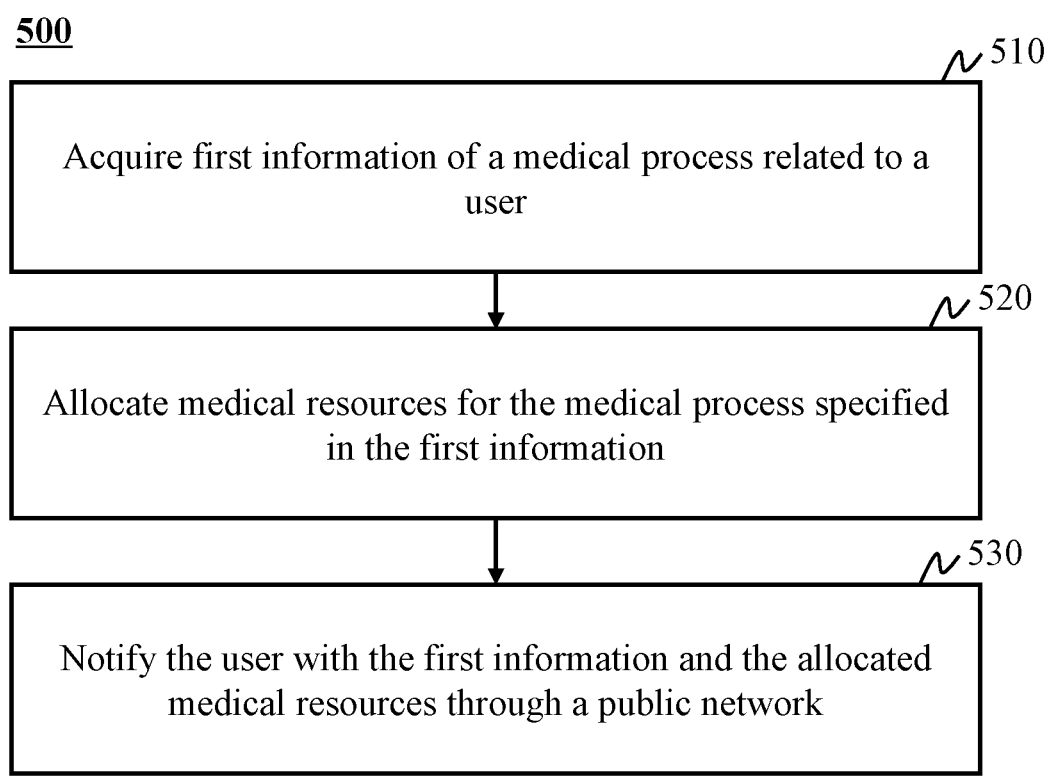
FIG. 5 is a schematic diagram illustrating an exemplary process for the medical resources allocation according to some embodiments of the present disclosure.

FIG. 5 is a schematic diagram illustrating an exemplary process for the medical resources allocation according to some embodiments of the present disclosure. Process 500 may be an exemplary embodiment of the process 400. Process 500 may be performed by the medical resources allocation device 140 for allocating medical resources of one or more medical resources providers (e.g., medical resources providers 110~113) for a medical process of a user 135 (e.g., a patient). In some embodiments, one or more operations of process 500 illustrated in FIG. 5 for medical resources allocation may be implemented in the medical resources allocation system illustrated in FIGS. 1-A and 1-B. For example, the process 500 illustrated in FIG. 5 may be stored in the storage 150 in the form of instructions, and invoked and/or executed by the medical resources allocation device 140 (e.g., the processor 210 of the computing device 200 as illustrated in FIG. 2-A). One or more operations of the process 500 may be executed by one or more sub-modules of the medical resources allocation device 140.

In 510, the acquisition module 310 may acquire information on a medical process (first information) related to the user 135. In 520, the allocation module 320 may allocate medical resources for the medical process specified in the first information. Operations 510 and 520 may be the same as or similar to operations 410 and 420 of process 400 described in connection with FIG. 4, the descriptions of which are not repeated here.

In 530, the first notification module 330 may notify the user 350 with the first information and the allocated medical resources through a public network (e.g., the network 120). For example, the first notification module 330 may forward the appointment information of one or more sub-processes of the medical process of the user 135. The first notification module 330 may forward the information automatically (e.g., once the information becomes available, periodically) or in response to an instruction of another user 135 (e.g., a doctor, a nurse, an assistant of the medical resources provider(s)).

In some embodiments, the first notification module 330 may cause an overview of the sub-processes and/or items of the medical process including all the related information to be displayed on a webpage or an interface (e.g., software, application). The webpage or the interface may be displayed via a private terminal device 130 of the user 135 or a public electric bulletin board. The related information may include information on some or all the sub-processes of the medical process. The related information may further include information on allocated medical resources corresponding to the sub-processes. Each allocated medical may be displayed beside the corresponding sub-process. A user 135 may have an intuitional view of at least part of or the entire medical process displayed in this manner. The user 135 may also determine the contents he would like to look into based on his own need.

Figure 6:
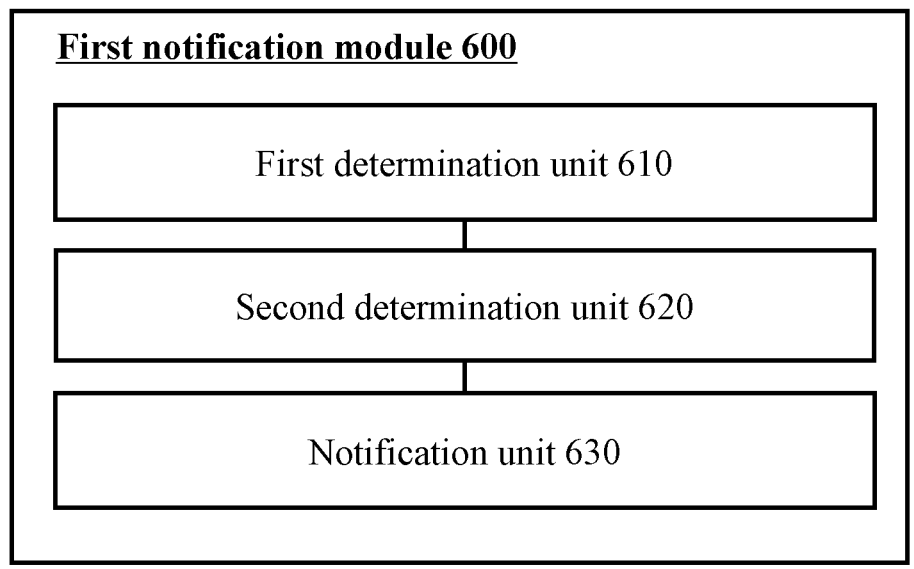
FIG. 6 is a schematic diagram illustrating an exemplary first notification module according to some embodiments of the present disclosure.

FIG. 6 is a schematic diagram illustrating an exemplary first notification module according to some embodiments of the present disclosure. The first notification module 600 may be an exemplary embodiment of the first notification module 330. The first notification module 600 may include a first determination unit 610, a second determination unit 620, and a notification unit 630. The first determination unit 610 may be configured to determine at least one key time point for each of sub-processes of the medical process based on the first information. The second determination unit 620 may be configured to determine, based on a current sub-process of the user 135 from the at least one key time point, a closest time node after the current sub-process. The notification unit 630 may notify the user with information on the sub-process corresponding to the closest time node and the allocated medical resource corresponding to the sub-process at a time point related to the closest time node (e.g., right at the closet time node, 5 min before the closet time node, 10 min before the closet time node). The first notification module 600 may perform one or more operations of process 600 illustrated in FIG. 6 for notifying the user with the first information and the corresponding medical resources.

Figure 7:
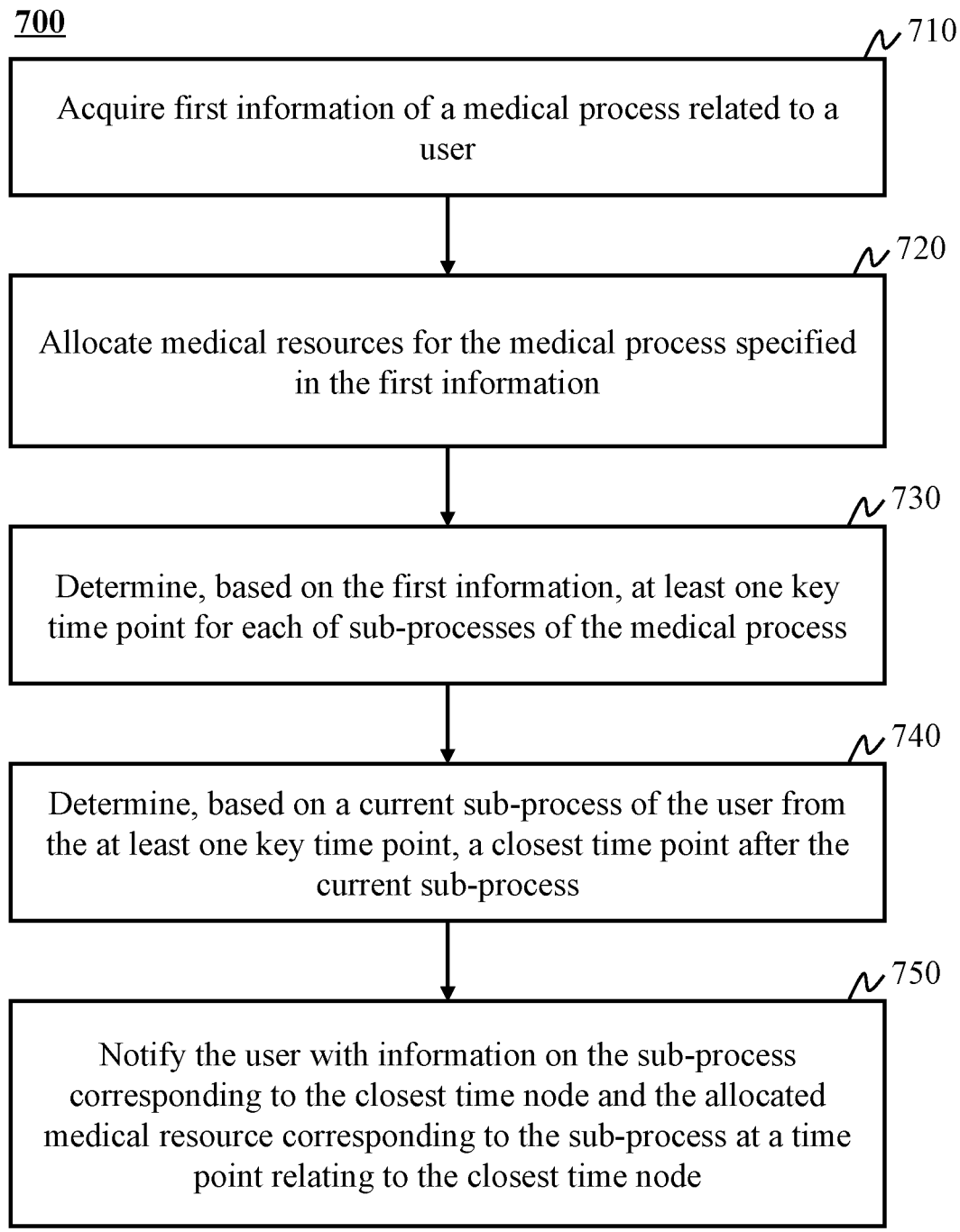
FIG. 7 is a schematic diagram illustrating an exemplary process for notifying a user with the first information and the allocated medical resources according to some embodiments of the present disclosure.

FIG. 7 is a schematic diagram illustrating an exemplary process for notifying a user with the first information and the allocated medical resources according to some embodiments of the present disclosure. Process 700 may be an exemplary embodiment of the process 400. Process 700 may be performed by the medical resources allocation device 140 for allocating medical resources of one or more medical resources providers (e.g., medical resources providers 110~113) for a medical process of a user 135 (e.g., a patient). In some embodiments, one or more operations of process 700 illustrated in FIG. 7 for medical resources allocation may be implemented in the medical resources allocation system illustrated in FIGS. 1-A and 1-B. For example, the process 700 illustrated in FIG. 7 may be stored in the storage 150 in the form of instructions, and invoked and/or executed by the medical resources allocation device 140 (e.g., the processor 210 of the computing device 200 as illustrated in FIG. 2-A). One or more operations of the process 700 may be executed by one or more sub-modules of the medical resources allocation device 140.

In 710, the acquisition module 310 may acquire information on a medical process (first information) related to the user 135. In 720, the allocation module 320 may allocate available medical resources for the medical process specified in the first information. Operations 710 and 720 may be the same as or similar to operations 410 and 420 of process 400 described in connection with FIG. 4, the description of which is not repeated here.

Operations 730 to 750 may be performed by the first notification module 330 (e.g., the exemplary first notification module 600). Operations 430 may be achieved by operations 730 through 750.

In 730, the first determination unit 610 may determine at least one key time point for each of sub-processes of the medical process based on the first information. The at least one key time point may relate to a start time, an ending time, etc., of a corresponding sub-process. One sub-process may include one or more key time points. In some embodiments, the one or more key time points may relate to a progress of a current sub-process or a progress of the medical process (e.g., 0%, 10%, 50%, 80%, 100%).

In 740, the second determination unit 620 may determine, based on a current sub-process (or a current progress of the medical process) of the user, a closet time point from the at least one key time point after the current sub-process (or the current progress of the medical process). In some embodiments, the second determination unit 620 may identify or recognize the current sub-process based on the current time and the time arrangement of the medical process. The second determination unit 620 may then determine or identify an upcoming sub-process based on the first information and one or more related key time points. The second determination unit 620 may select a key time point indicating a time closest to the current time from the one or more key time points related to the next sub-process.

In 750, the notification unit 630 may notify the user 135 with information on the sub-process corresponding to the closest time point and the allocated medical resource corresponding to the sub-process at a time point (notification time point) related to the closest time point (e.g., the closest time point, a time point before the closest time point with a predetermined time interval). For example, the notification unit 630 may provide and transmit the first data corresponding to the appointment information of the sub-process to the terminal device 130 of the user 135 at the notification time point.

Figure 8:
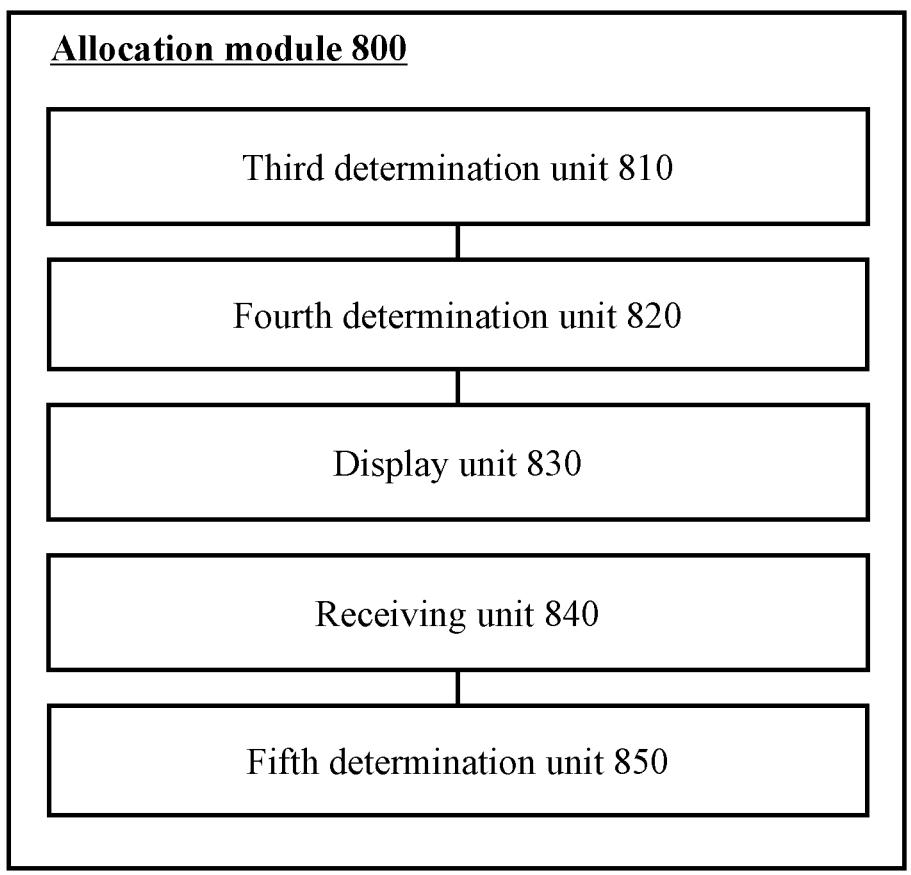
FIG. 8 is a schematic diagram illustrating an exemplary allocation module according to some embodiments of the present disclosure.

FIG. 8 is a schematic diagram illustrating an exemplary allocation module according to some embodiments of the present disclosure. Allocation module 800 may be an exemplary embodiment of the allocation module 320. The allocation module 800 may include a third determination unit 810, a fourth determination unit 820, a display unit 830, a receiving unit 840, and a fifth determination unit 850.

The third determination unit 810 may be configured to determine, based on the first information, information on a sub-process of the plurality of sub-processes of the medical process specified in the first information. The fourth determination unit 820 may be configured to identify a plurality of available medical resources corresponding to the sub-process. The display unit 830 may be configured to cause information on the plurality of available medical resources to be displayed on an interface of the terminal device 130. The receiving unit 840 may be configured to receive a request for selecting a medical resource from the plurality of available medical resources. The fifth determination unit 850 may be configured to allocate, in response to the received request, the selected medical resources indicated by the received request to the sub-process and generate an allocation result therefrom.

Figure 9:
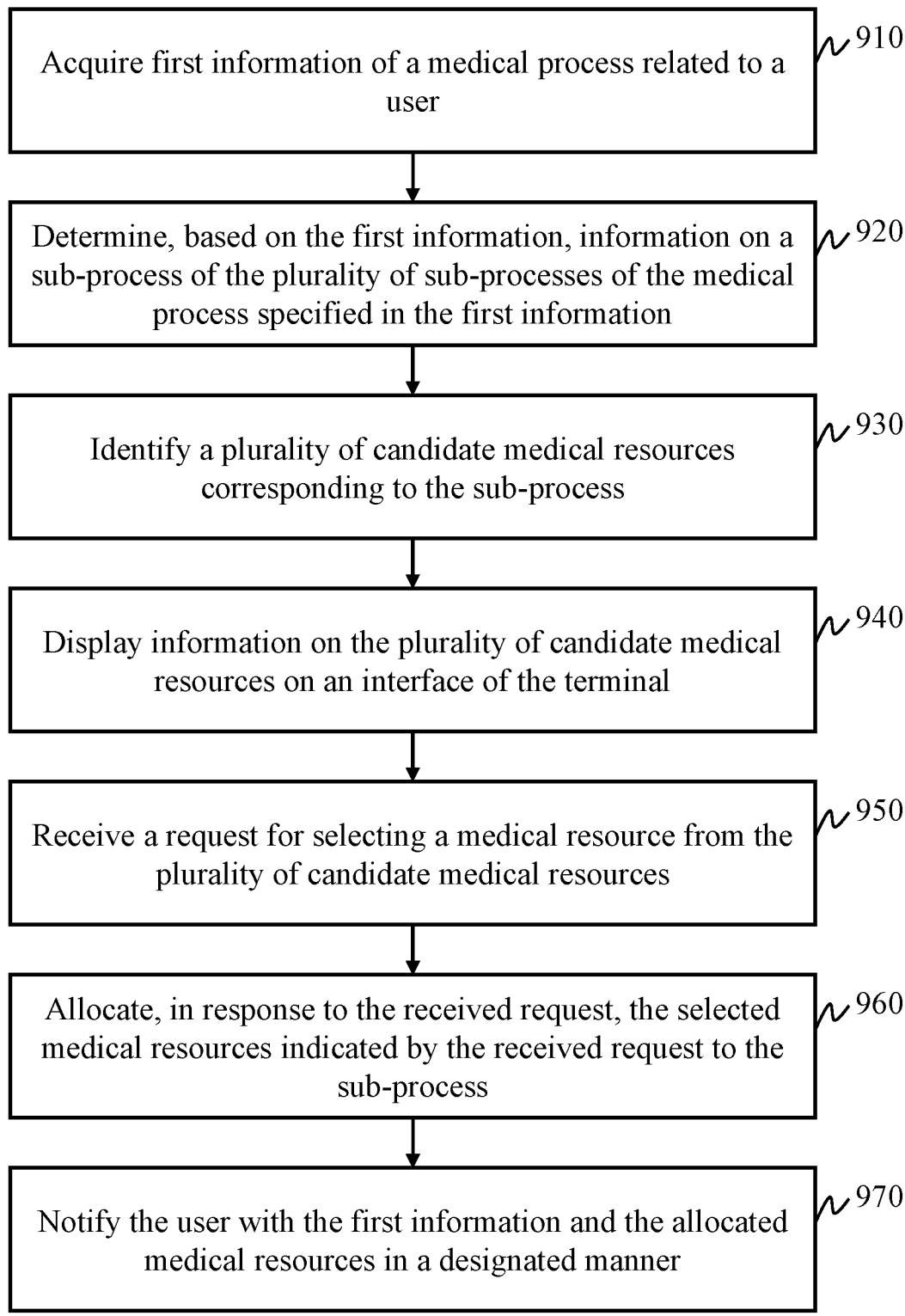
FIG. 9 is a schematic diagram illustrating an exemplary process of medical resources allocation according to some embodiments of the present disclosure.

The allocation module 800 may perform one or more operations of process 900 illustrated in FIG. 9 for allocating available medical resources to the medical process of the user 135.

FIG. 9 is a schematic diagram illustrating an exemplary process of medical resources allocation according to some embodiments of the present disclosure. Process 900 may be an exemplary embodiment of the process 400. Process 900 may be performed by the medical resources allocation device 140 for allocating medical resources of one or more medical resources providers (e.g., medical resources providers 110~113). In some embodiments, one or more operations of process 900 illustrated in FIG. 9 for medical resources allocation may be performed by the medical resources allocation system illustrated in FIGS. 1-A and 1-B. For example, the process 900 illustrated in FIG. 9 may be stored in the storage 150 in the form of instructions, and invoked and/or executed by the medical resources allocation device 140 (e.g., the processor 210 of the computing device 200 as illustrated in FIG. 2-A). One or more operations of the process 900 may be executed by one or more sub-modules of the medical resources allocation device 140.

In 910, the acquisition module 310 may acquire information on a medical process (first information) related to a user 135 (e.g., a patient). Operation 910 may be the same as or similar to operation 410 of process 400 described in connection with FIG. 4, the descriptions of which are not repeated here.

Operations 920 to 960 may be performed by the allocation module 800, which is an exemplary embodiment of the allocation module 320. Operation 420 may be achieved by operations 920-960.

In 920, the third determination unit 810 may determine based on the first information, information on a sub-process of the plurality of sub-processes of the medical process specified in the first information.

In 930, the fourth determination unit 820 may determine or identify a plurality of candidate medical resources corresponding to the sub-process. The fourth determination unit 820 may determine or identify the plurality of candidate medical resources based on the first information (e.g., the first time information) and the second information as described in connection with FIG. 4. The determined plurality of candidate medical resources may be available during the schedule time slot of the sub-process. In some embodiments, the fourth determination unit 820 may identify the available medical resources based further on distances between a location designated the user 135 and the locations of medical resources (e.g., locations of medical resources providers).

In 940, the display unit 830 may cause information on the plurality of candidate medical resources to be displayed on an interface (e.g., provided by the medical plan arrangement application) of the terminal device 130. For example, the display unit 830 may provide and transmit third data to the terminal device via the network 120. The third data may correspond to the plurality of candidate medical resources determined in 930 and may cause the terminal device 130 to generate a fourth presentation (e.g., an interface) on the display of the terminal device. The fourth presentation may include the plurality of candidate medical resources and concurrently provide a third user interface feature. The plurality of candidate medical resources may be displayed in the form of, for example, a list, a drop-down menu, a text box, a dialog box, a check box, icons, or the like, or a combination thereof, on the fourth presentation.

In some embodiments, the display unit 830 may encrypt the third data and provide the encrypted third data to the terminal device 130 (or the medical plan arrangement application) for generating the fourth presentation, so as to protect the privacy of the user 135.

In 950, the receiving unit 840 may receive a request (or be referred to as a selection request) for selecting a medical resource from the plurality of candidate medical resources. Besides the displayed candidate medical resources, the fourth presentation may concurrently provide a third user interface feature from which the user can select a medical resource or a set of medical resources for the sub-process from the plurality of candidate medical resources. The third user interface feature may be in the form of a drop-down menu, a dialog box, one or more buttons or icons, or the like, or a combination thereof. In some embodiments, the third user interface feature may also be used to display the plurality of candidate medical resources. For example, the user may select a medical resource by interacting with a pull-down menu or a check box displaying the plurality of candidate medical resources.

By interacting with the third user interface feature, the user 135 may select a medical resource (or a set of medical resources) as an aforementioned target medical resource for the sub-process and trigger a transmission of a selection request (encrypted or not encrypted) to the medical resources allocation device 140. The selection request may include or indicate the selected medical resource.

In 960, the fifth determination unit 850 may allocate or assign, in response to the received request (selection request), the selected medical resource (or target medical resource) indicated by the received request to the sub-process.

In 970, the first notification module 330 may notify the user with the first information and the allocated medical resources in a designated manner. Operation 970 may be the same as or similar to operation 430 described in connection with FIG. 4, operation 530 described in connection with FIG. 5, or operations 720 to 750 described in connection with FIG. 7, the descriptions of which are not repeated herein.

FIG. 10 is a schematic diagram illustrating an exemplary medical resources allocation device according to some embodiments of the present disclosure. The medical resources allocation device 1000 may be an exemplary embodiment of the medical resources allocation device 140. The medical resources allocation device 1000 may include an acquisition module 1010, an allocation module 1020, a first notification module 1030, a receiving module 1040, a determination module 1050, and a second notification module 1060. The medical resource allocation device 1000 may further facilitate the user 135 searching for information related to the medical process and allocated medical resources.

The acquisition module 1010 may have a function that is the same as or similar to that of the acquisition module 310. The allocation module 1020 may have a function that is the same as or similar to that of the allocation module 320 or 800. The first notification module 1030 may have a function that is the same as or similar to that of the first notification module 330 or 600.

The receiving module 1040 may be configured to receive, from the user 135, a search request including time information. The determination module 1050 may be configured to determine, based on the time information, an objective sub-process corresponding to the time information and an allocated medical resource corresponding to the objective sub-process. The second notification module 1060 may be configured to notify the user with information on the objective sub-process and the allocated medical resource corresponding to the objective sub-process.

The medical resources allocation device 1000 may perform one or more operations of process 400 illustrated in FIG. 4, process 500 illustrated in FIG. 5, process 700 illustrated in FIG. 7, and process 900 illustrated in FIG. 9. The medical resources allocation device 1000 may further perform process 1100 illustrated in FIG. 11

Figure 11:
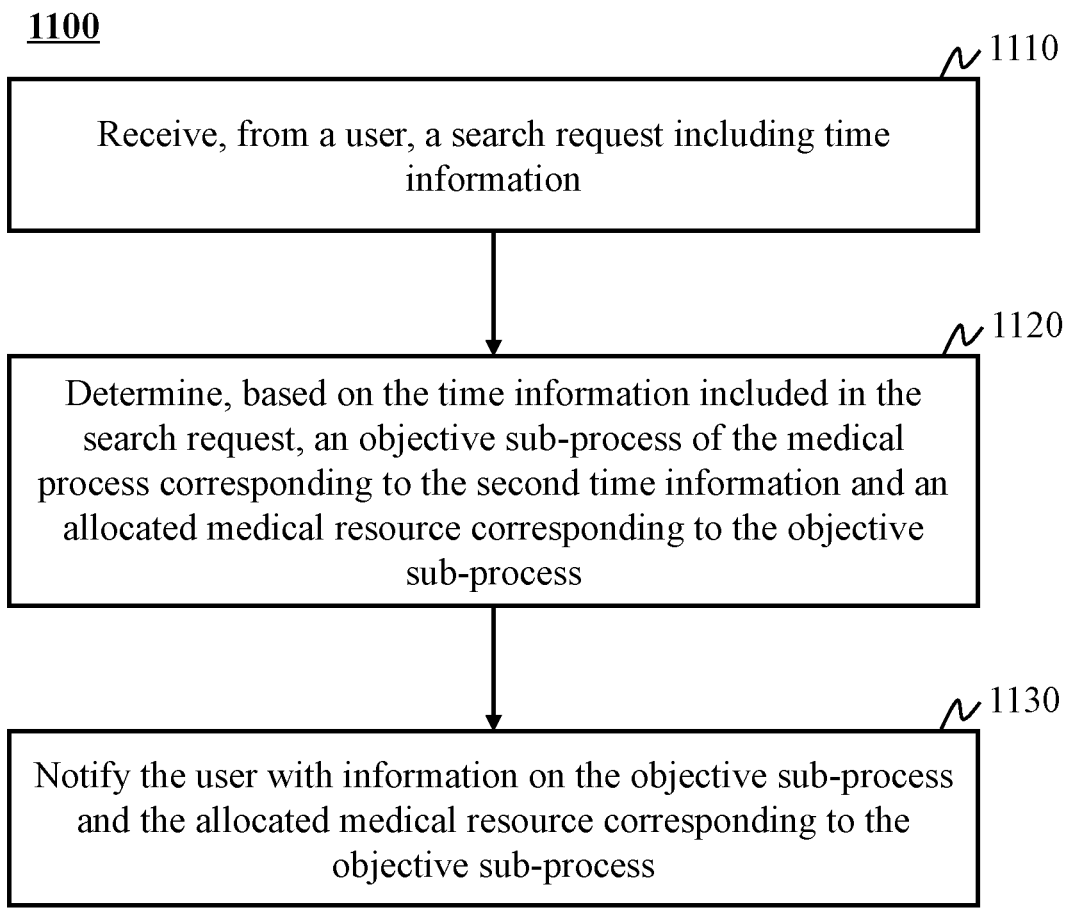
FIG. 11 is a schematic diagram illustrating an exemplary process for searching for information related to the medical process and allocated medical resources according to some embodiments of the present disclosure

FIG. 11 is a schematic diagram illustrating an exemplary process for searching for information related to the medical process and allocated medical resources according to some embodiments of the present disclosure. In some embodiments, one or more operations of process 1100 illustrated in FIG. 11 for searching for information may be performed by the medical resources allocation system illustrated in FIGS. 1-A and 1-B. For example, the process 1100 illustrated in FIG. 11 may be stored in the storage 150 in the form of instructions, and invoked and/or executed by the medical resources allocation device 1000 (e.g., the processor 210 of the computing device 200 as illustrated in FIG. 2-A). One or more operations of the process 1100 may be executed by one or more sub-modules of the medical resources allocation device 1000.

In 1110, the receiving module 1040 may receive, from a user 135, a search request including time information. The user 135 may send the search request via a search interface (e.g., provided by the medical process arrangement application) on the terminal device 130 through the network 120 to the medical resources allocation device 1000. In some embodiments, the time information may also be identified by the names or labels of the sub-processes of the medical process.

In 1120, the determination module 1050 may determine, based on the time information included in the search request, an objective sub-process corresponding to the time information and an allocated medical resource (or a set of allocated medical resources) corresponding to the objective sub-process. The time information may be input by the user 135 for searching information on a sub-process (or multiple sub-processes) corresponding to a time point or a time slot indicated by the time information and/or information on allocated medical resources corresponding to the objective sub-process. For example, the sub-process may be performed at or right after the time point, or during the time slot, indicated by the time information. In some embodiments, the determination module may determine the sub-process and/or the allocated medical resource further based on the first time information included in the first information.

In 1130, the second notification module 1060 may notify the user 135 with information on the objective sub-process and the allocated medical resource corresponding to the objective sub-process (e.g., via a corresponding first presentation). The notification manner of the objective sub-process may be the same as or similar to the notification manners described in connection with the operation 430 of FIG. 4 and not repeated herein.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A computer-implemented method to provide medical services to a user, the method comprising:
    acquiring, by one or more servers, first information for identifying a medical process associated with a medical plan arrangement application being executed on a mobile computing device, wherein the medical process includes a plurality of sub-processes and the first information includes a list of the plurality of sub-processes, a sequence of the plurality of sub-processes, a schedule time slot for a sub-process, and a place of a visit of a sub-process, wherein the schedule time slot for the sub-process is determined based on a priority factor assigned to the sub-process,
    communicating, by the one or more servers, with the medical plan arrangement application to receive a medical resource allocation request;
    after receiving the medical resource allocation request, initiating, by the one or more servers, a medical resource allocation process according to the sequence of the plurality of sub-processes by programmatically executing:
        for each sub-process of at least some of the plurality of sub-processes:
            determining, based at least on the first information, a schedule time slot of the sub-process;
            determining, from the medical resources based at least on the second information, one or more candidate medical resources that satisfy a criterion of being available during the schedule time slot of the sub-process;
            selecting a target medical resource from the one or more candidate medical resources based on costs of the one or more candidate medical resources, wherein a cost of each of the one or more candidate medical resources is determined based on a combination of a time cost, a travel cost, and a financial cost, the target medical resource has a minimum cost among the one or more candidate medical resources, and the time cost is a waiting time to a start time point of an available time slot of a candidate medical resource; and
            assigning the target medical resource to the sub-process;
        for at least one sub-process of the plurality of sub-processes that is assigned a selected medical resource, executing, by the one or more servers, a notification process of the at least one sub-process, wherein the sequence of the plurality of sub-processes is determined based on a time sequence of available time slots of the medical resources associated with the sub-processes, an available time slot of a target medical resource to a sub-process is closest to an attendance time slot of a sub-process prior to the sub-process among the available time slots; and
        receiving from the mobile computing device, a navigation request; and
    after receiving the navigation request, initiating, by the one or more servers, the navigation process by programmatically executing:
        determining, based on location data determined by the medical plan arrangement application executing to interface with a positioning module of the mobile computing device, a current location of the mobile computing device;
        determining, based on the second information, the location of the assigned medical resource of the at least one sub-process;
        determining a route from the current location of the mobile computing device to the location of the medical resource assigned to the at least one sub-process; and
        providing navigation data to the medical plan arrangement application being executed on the mobile computing device to generate a second presentation including a map on the display of the mobile computing device.

2. The method of claim 1, wherein the communicating with the medical plan arrangement application being executed on the mobile computing device to receive a medical plan arrangement request includes:
    encrypting second data regarding the medical process to be sent to the medical plan arrangement application;
    providing the encrypted second data to the medical plan arrangement application being executed on the mobile computing device to generate a third presentation on the display of the mobile computing device, wherein the third presentation depicts the medical process related to the patient and provides a second user interface feature from which the user can trigger transmission of the medical plan arrangement request to the one or more servers; and
    receiving, from the mobile computing device, the medical plan arrangement request after the user interacts with the second user interface feature.

3. The method of claim 1, further comprising:
    determining an upcoming sub-process of the medical process as the at least one sub-process of the plurality of sub-processes for which the notification process is to be executed; and
    determining a notification time point before an attendance time slot of the upcoming sub-process with a predetermined time interval, wherein the notification process of the upcoming sub-process is executed at the notification time point.

4. The method of claim 1, wherein:
    the second information further includes locations of the medical resources; and
    the method further comprises:
        determining a location associated with the user; and
        determining distances from the location associated with the user to the locations of the medical resources, wherein the target medical resource is selected based at least on the determined distances.

5. The method of claim 1, wherein the selecting a target medical resource from the one or more candidate medical resources comprises:
    encrypting third data regarding the one or more candidate medical resources to be sent to the medical plan arrangement application;

providing encrypted third data to the mobile computing device via the network, causing the mobile computing device to generate a fourth presentation on a display of the mobile computing device, wherein the fourth presentation includes the one or more candidate medical resources corresponding to the sub-process and concurrently provides a third user interface feature from which the user can select a medical resource as the target medical resource from the one or more candidate medical resources and trigger a transmission of a selection request including the target medical resource; and receiving the selection request from the mobile computing device.

6. The method of claim 1, further comprising:

receiving, from the mobile computing device through the network, a search request including time information; and searching, in response to the received search request, an objective sub-process from the plurality of sub-processes based on the time information as the at least one sub-process of the plurality of sub-processes of which the notification process is to be executed.

7. The method of claim 1, wherein:

the medical resource allocation process is executed based on one or more first rules of a rulebook; and the method further comprises, when a sub-process of the plurality of sub-processes is failed to be allocated with a medical resource via the medical resource allocation process based on the one or more first rules:

retrieving one or more second rules from the rulebook; and continuing to execute the medical resource allocation process for the sub-process based at least on the one or more second rules.

8. A method for operating one or more servers to provide medical services to a user, the method comprising:

acquiring, by the one or more servers, first information of a medical process from a first storage device, wherein the medical process includes a plurality of sub-processes to be allocated with medical resources and the first information includes a list of the plurality of sub-processes, a sequence of the plurality of sub-processes, a schedule time slot for a sub-process, and a place of a visit of a sub-process, wherein the schedule time slot for the sub-process is determined based on a priority factor assigned to the sub-process;

obtaining, by the one or more servers, second information on medical resources from a second storage device, the second storage device providing medical resource information of one or more medical resource providers, wherein the second information includes available time slots and locations of the medical resources;

allocating, by the one or more servers, the medical resources for the medical process based on the first information and the second information according to the sequence of the plurality of sub-processes, including for each sub-process of at least some of the plurality of sub-processes:

determining, based at least on the first information, a schedule time slot of the sub-process;

determining, from the medical resources based at least on the second information, one or more candidate medical resources that satisfy a criterion of being available during the schedule time slot of the sub-process;

selecting a target medical resource from the one or more candidate medical resources based on costs of the one or more candidate medical resources, wherein a cost of each of the one or more candidate medical resources is determined based on a combination of a time cost, a travel cost, and a financial cost, the target medical resource has a minimum cost among the one or more candidate medical resources, and the time cost is a waiting time to a start time point of an available time slot of a candidate medical resource; and assigning the target medical resource to the sub-process as the allocated medical resource of the sub-process, wherein the sequence of plurality of the sub-processes is determined based on a time sequence of available time slots of the medical resources associated with the sub-processes, an available time slot of a target medical resource to a sub-process is closest to an attendance time slot of a sub-process prior to the sub-process among the available time slots;

determining, by the one or more servers, for at least one sub-process of the plurality of sub-processes of the medical process, appointment information of the at least one sub-process based on at least a portion of the second information corresponding to the medical resource allocated to the at least one sub-process, wherein the appointment information of the at least one sub-process is for presentation on a user interface of a mobile computing device; and notifying, by the one or more servers via a network, the user with the appointment information of the at least one sub-process of the plurality of sub-processes.

9. The method of claim 8, further comprising:

determining an upcoming sub-process of the medic process as the at least one sub-process of the plurality of sub-processes whose appointment information is to be notified;

determining a notification time point based on a closest time point associated with the upcoming sub-process; and notifying the user by sending to the mobile computing device via the network the appointment information of the upcoming sub-process for presentation on the user interface at the notification time node.

10. The method of claim 8, wherein the notifying the user with the appointment information of the at least one sub-process of the plurality of sub-processes comprises:

providing first data corresponding to the appointment information of the at least one sub-process of the plurality of sub-processes; and transmitting the first data to the mobile computing device via the network, wherein:

the first data causes the mobile computing device to generate a first presentation on a display of the mobile computing device; and the first presentation includes the appointment information of the at least one sub-process of the plurality of sub-processes.

11. The method of claim 10, further comprising:

determining a location associated with the user;

determining distances from the location associated with the user to the locations of the medical resources, wherein the allocating the medical resources for the medical process is based further on the determined distances.

12. The method of claim 10, further comprising:
determining, based on location data received from the mobile computing device via the network, a current location of the mobile computing device;
determining, based on the second information, a location of the allocated medical resource included in the first presentation;
determining a route from the current location of the mobile computing device to the location of the allocated medical resource; and
providing navigation data including the route to the mobile computing device to generate a second presentation including a map on the display of the mobile computing device, wherein the second presentation depicts: (i) the current location of the mobile computing device on the map, (ii) the location of the allocated medical resource on the map, and (iii) the route on the map.

13. The method of claim 10, wherein the selecting a target medical resource from the one or more candidate medical resources comprises:
transmitting third data to the mobile computing device via the network, causing the mobile computing device to generate a fourth presentation on a display of the mobile computing device, wherein the fourth presentation includes the one or more candidate medical resources corresponding to the at least one sub-process and concurrently provides a user interface feature from which the user can select a medical resource as the target medical resource from the one or more candidate medical resources and trigger a transmission of a selection request including the target medical resource; and
receiving the selection request from the mobile computing device.

14. The method of claim 8, wherein:
the medical resources are allocated for the medical process based further on one or more first rules of a rulebook; and
the method further comprising, when a sub-process of the plurality of sub-processes is failed to be allocated with a medical resource based on the one or more first rules:
retrieving one or more second rules from the rulebook; and
continuing to allocate medical resources for the sub-process based at least on the one or more second rules.

15. The method of claim 10, further comprising:
receiving, from the mobile computing device through the network, a search request including time information;
searching, in response to the received search request, an objective sub-process from the plurality of sub-processes based on the time information as the at least one sub-process of the plurality of sub-processes of which the appointment information is to be notified.

16. A system for providing medical services to a user, the system comprising:
one or more network interfaces to communicate with a mobile computing device of the user; and
one or more processors in communication with the one or more network interfaces, the one or more processors to:
acquire first information for identifying a medical process, wherein the medical process includes a plurality of sub-processes and the first information includes a list of the plurality of sub-processes, a sequence of the plurality of sub-processes, a schedule time slot for a sub-process, and a place of a visit of a sub-process, wherein the schedule time slot for the sub-process is determined based on a priority factor assigned to the sub-process;
acquire, from at least one storage device, second information on medical resources of a plurality of medical resource providers, wherein the second information includes available time slots of the medical resources;
communicate with the medical plan arrangement application being executed on the mobile computing device to receive a medical resource allocation request;
initiate, after receiving the medical resource allocation request, a medical resource allocation process according to the sequence of the plurality of sub-processes by programmatically executing:
for each sub-process of at least some of the plurality of sub-processes:
determining, based at least on the first information, a schedule time slot of the sub-process;
determining, from the medical resources based at least on the second information, one or more candidate medical resources that satisfy a criterion of being available during the schedule time slot of the sub-process;
selecting a target medical resource from the one or more candidate medical resources based on costs of the one or more candidate medical resources, wherein a cost of each of the one or more candidate medical resources is determined based on a combination of a time cost, a travel cost, and a financial cost, the target medical resource has a minimum cost among the one or more candidate medical resources, and the time cost is a waiting time to a start time point of an available time slot of a candidate medical resource; and
assigning the target medical resource to the sub-process, wherein the sequence of the plurality of sub-processes is determined based on a time sequence of available time slots of the medical resources associated with the sub-processes, an available time slot of a target medical resource to a sub-process is closest to an attendance time slot of a sub-process prior to the sub-process among the available time slots;
execute, for at least one sub-process of the plurality of sub-processes that is assigned a selected medical resource, a notification process of the at least one sub-process
receiving, from the mobile computing device, a navigation request; and
initiate, after receiving the navigation request, the navigation process by programmatically executing:
determining, based on location data determined by the medical plan arrangement application executing to interface with a positioning module of the mobile computing device, a current location of the mobile computing device;
determining, based on the second information, the location of the assigned medical resource of the at least one sub-process;
determining a route from the current location of the mobile computing device to the location of the medical resource assigned to the at least one sub-process; and
providing navigation data to the medical plan arrangement application being executed ing on the mobile computing device to generate a second presentation including a map on the display of the mobile computing device, wherein the second presentation depicts.

17. The system of claim 16, wherein:

the second information further includes locations of the medical resources; and the one or more processors further to:
- determine a location associated with the user;
- determine distances from the location associated with the user to the locations of the medical resources, wherein the target medical resource is selected based at least on the determined distances.

18. The system of claim 16, wherein:

the medical resource allocation process is executed based on one or more first rules of a rulebook; and the one or more processors further to, when a sub-process of the plurality of sub-processes is failed to be allocated with a medical resource via the medical resource allocation process based on the one or more first rules:
- retrieve one or more second rules from the rulebook; and
- continue to execute the medical resource allocation process for the sub-process based at least on the one or more second rules.

19. The system of claim 16, wherein to select a target medical resource from the one or more candidate medical resources, the one or more processors to:
- encrypt third data regarding the one or more candidate medical resources to be sent to the medical plan arrangement application;
- provide encrypted third data to the mobile computing device via the network, causing the mobile computing device to generate a fourth presentation on a display of the mobile computing device, wherein the fourth presentation includes the one or more candidate medical resources corresponding to the sub-process and concurrently provides a third user interface feature from which the user can select a medical resource as the target medical resource from the one or more candidate medical resources and trigger a transmission of a selection request including the target medical resource; and
- receive the selection request from the mobile computing device.

20. The system of claim 16, where the notification process includes:
- determining an upcoming sub-process of the medical process as the at least one sub-process of the plurality of sub-processes for which the notification process is to be executed; and
- determining a notification time point before an attendance time slot of the upcoming sub-process with a predetermined time interval, wherein the notification process of the upcoming sub-process is executed at the notification time point.

* * * * *